(12) United States Patent
Glazer et al.

(10) Patent No.: US 7,169,582 B2
(45) Date of Patent: *Jan. 30, 2007

(54) MULTIFUNCTIONAL RECOMBINANT PHYCOBILIPROTEIN-BASED FLUORESCENT CONSTRUCTS AND PHYCOBILISOME DISPLAY

(75) Inventors: Alexander N. Glazer, Berkeley, CA (US); Yuping Cai, Indianapolis, IN (US)

(73) Assignee: Regents of the University of California, Oakland, CA (US)

(*) Notice: Subject to any disclaimer, the term of this patent is extended or adjusted under 35 U.S.C. 154(b) by 544 days.

This patent is subject to a terminal disclaimer.

(21) Appl. No.: 10/617,208

(22) Filed: Jul. 10, 2003

(65) Prior Publication Data

US 2004/0009559 A1    Jan. 15, 2004

Related U.S. Application Data

(62) Division of application No. 09/469,194, filed on Dec. 21, 1999, now Pat. No. 6,649,376.

(51) Int. Cl.
    C12N 15/09    (2006.01)
    C12N 1/20     (2006.01)
    C07K 14/00    (2006.01)

(52) U.S. Cl. .............. 435/69.7; 435/69.1; 435/320.1; 435/252.1; 435/7.7; 530/350; 536/23.1; 436/501

(58) Field of Classification Search ............ 435/69.7, 435/69.1, 320.1, 252.1, 7.7; 530/350; 536/23.1; 436/501

See application file for complete search history.

(56) References Cited

U.S. PATENT DOCUMENTS 4,520,110 A    5/1985    Stryer et al.
5,055,556 A    10/1991   Stryer et al.

FOREIGN PATENT DOCUMENTS

WO    98/23737    6/1998
WO    01/96871    12/2001

OTHER PUBLICATIONS

Database CA Online!, Chemical Abstracts Service, Qin, Song et al., retrieved from STN Database Accession No. 132:19595 HCA.
Mosley, David et al., Nov. 5, 1997, Photochemistry and Photobiology 66(5):710-15.
Cherry, Richard et al., Jan. 12, 1998, Journal of Cell Biology 140(1):71-79.
Cai, Yuping et al., Mar. 15, 2001, Analytical Biochemistry 290(2):186-204.
The University of Tulsa Graduate School Dissertation by Colleen Mary Tool, Process and Structure in the Assembly of a Cyanobacterial Light-Harvesting Complex, UMI No. 9839498.
Abstract: UMIProQuest Publication No. AAT 9839498, Toole, Colleen Mary, Process and Structure in the Assembly of a Cyanobacterial Light-Harvesting Complex, Jan. 1999.

*Primary Examiner*—Chih-Min Kam
(74) *Attorney, Agent, or Firm*—Richard Aaron Osman

(57) ABSTRACT

The invention provides multifunctional fusion constructs which are rapidly incorporated into a macromolecular structure such as a phycobilisome such that the fusion proteins are separated from one another and unable to self-associate. The invention provides methods and compositions for displaying a functional polypeptide domain on an oligomeric phycobiliprotein, including fusion proteins comprising a functional displayed domain and a functional phycobiliprotein domain incorporated in a functional oligomeric phycobiliprotein. The fusion proteins provide novel specific labeling reagents.

19 Claims, No Drawings

MULTIFUNCTIONAL RECOMBINANT PHYCOBILIPROTEIN-BASED FLUORESCENT CONSTRUCTS AND PHYCOBILISOME DISPLAY

CROSS-REFERENCE TO RELATED APPLICATION

This application is a divisional of and claims priority under 35 U.S.C. § 120 to U.S. Ser. No. 09/469,194, filed Dec. 21, 1999, now U.S. Pat. No. 6,649,376, having the same title and inventors, which is incorporated herein by reference.

The research carried out in the subject application was supported in part by grants from the Department of Energy (Grant No. RDE-FG-91ER61125). The government may have rights in this invention.

INTRODUCTION

1. Field of the Invention

The field of the invention is phycobiliprotein-assisted expression and folding of proteins and the production of function-added recombinant phycobiliproteins.

2. Background of the Invention

Many foreign proteins expressed in bacteria form insoluble aggregates called inclusion bodies. Recovery of the recombinant protein of interest requires dissolving the inclusion bodies under denaturing conditions, removing the denaturant to allow the recombinant protein to fold, and finally purifying the recombinant protein. This process is laborious and frequently gives low yields. Inclusion bodies are formed because the aggregation of the newly synthesized recombinant polypeptide is faster than its folding into the native structure. In one aspect, the invention provides bifunctional fusion constructs which are rapidly incorporated into a macromolecular structure such that the fusion proteins are separated from one another and unable to self-associate.

In a more particular aspect, the macromolecular structures are oligomeric phycobiliproteins—a family of structurally related photosynthetic accessory proteins naturally found, inter alia, in cyanobacteria, the chloroplasts of the Rhodophyta (red algae) and in those of the Cryptophyceae. When they carry covalently attached linear tetrapyrrole prosthetic groups (bilins), these proteins can exhibit brilliant colors and intense fluorescence, making them valuable specific labeling reagents. Unfortunately, the diversity of such reagents has been restricted to naturally occurring phycobiliproteins and their target specificity generated by chemical conjugation, which generates heterogeneity (see, e.g. Siiman et al., 1999, Bioconj Chem, 10, 1090–1106). The use of phycobiliproteins in the invention also overcomes these prior art limitations and provides homogenous, specific labeling reagents.

SUMMARY OF THE INVENTION

We have found that phycobiliprotein subunits are tolerant to terminal extensions of different sizes. A phycobiliprotein subunit domain in a fusion protein is able to assemble with to cognate partner subunit to form heterodimers, and frequently further assemble into even higher-order aggregates, and into the light-harvesting antenna complexes, phycobilisomes. The non-phycobiliprotein part of the fusion protein (the displayed domain) is exposed on the surface of the oligomeric phycobiliproteins. We define this fusion protein expression system as "phycobilisome display". Newly synthesized fusion polypeptides are quickly separated from each other by virtue of the assembly of the phycobiliprotein domain (the carrier domain) into oligomers. The non-phycobiliprotein moiety (the displayed domain) of the fusion protein is displayed on the surface of oligomer, e.g. the rods of the phycobilisome, and is able to fold into functional proteins while sequestered from interaction with other unfolded polypeptides. Phycobilisome display can therefore be used as an alternative folding environment for difficult-to-fold proteins, especially those that have been found difficult to fold in other organisms. The displayed protein can be used as a fusion construct bearing a fluorescent phycobiliprotein tag, or be separated from the carrier phycobiliprotein domain by cleavage of the linker peptide between the carrier domain and the displayed domain by a specific protease. Either embodiment may be practiced in cells (e.g. using a resident protease) or in vitro (e.g. using purified fusion proteins, cell-free expression systems, etc.), though cleavage is preferably practiced outside the cell to control its timing with respect to folding.

Accordingly, the invention provides methods and compositions for displaying a functional polypeptide domain on an oligomeric phycobiliprotein. The compositions include fusion proteins comprising a functional displayed domain and a functional phycobiliprotein domain incorporated in a functional oligomeric phycobiliprotein. In particular embodiments, the phycobiliprotein domain is a natural phycobiliprotein domain or modified variant thereof: the functional oligomeric phycobiliprotein is an $\alpha$, $\beta$ heterodimer; the displayed domain comprises an affinity tag, an oligomerization moiety, a specific binding moiety and/or a signaling moiety: and/or the displayed domain is refractive to expression in *E. coli*. The compositions also include functional oligomeric phycobiliproteins comprising the subject fusion proteins and cells comprising such oligomeric phycobiliproteins.

The subject methods include methods for making a functional displayed domain comprising the step of combining a polypeptide comprising a displayed domain and a phycobiliprotein domain with a phycobiliprotein subunit under conditions to form a subject fusion protein. In particular embodiments, the methods further comprise prior to the combining step, the step of making the polypeptide by expressing a nucleic acid encoding the polypeptide: and/or after the combining step, the step of separating the functional displayed domain from the functional phycobiliprotein domain. The methods steps may occur intracellularly, e.g. in a cell which is or is a progeny of a natural cell which naturally makes functional phycobiliprotein, or a cell engineered to produce functional phycobiliprotein.

DETAILED DESCRIPTION OF PARTICULAR EMBODIMENTS OF THE INVENTION

The following descriptions of particular embodiments and examples are offered by way of illustration and not by way of limitation.

The invention provides methods and compositions for displaying a functional polypeptide (the foreign protein or displayed domain) on an oligomeric phycobiliprotein. The compositions include fusion proteins comprising a functional displayed domain and a functional phycobiliprotein domain incorporated in a functional oligomeric phycobiliprotein.

A functional phycobiliprotein domain is capable of assembling the fusion protein in a functional oligomeric phycobiliprotein. Preferred domains provide at least 1%, preferably at least 10%, more preferably at least 50%, more preferably at least 75%, more preferably at least 90% and most preferably substantially equivalent oligomer assembly ability as that of a corresponding unfused phycobiliprotein, as measured in competition assays, e.g. as described herein.

Any phycobiliprotein domain having the requisite functionality may be used and these may be derived from natural, semisynthetic or synthetic sequences. A wide variety of natural phycobiliproteins are known in the art, e.g. Apt and Grossman, 1995, J Mol Biol 248, 79–96. including proteins derived from many cyanobacteria, rhodophytes (red algae) and cryptomonads. etc. (see, e.g. Glazer, 1994, J Appl Phycol 6, 105–112; Glazer et al. 1995, Photosynth Res 46, 93–105), particularly phycoerythrins, phycocyanins, and allophycocyanins. In addition, a wide variety of methods are known for modifying such natural sequences to generate semi-synthetics. e.g. Glazer, 1994, supra, describes phycobiliproteins having non-natural, predetermined bilin compositions, and exploiting intermolecular energy transfer by functionally coupling fluorescent phycobiliprotein tags with other fluorescent tags, such as cyanine dyes, and Toole et al., 1998, Mol Micro 30, 475–486 describes recombinations of phycobiliprotein deletion mutants. Finally, known phycobiliprotein structure-function relationships (e.g. Anderson et al., 1998, Mol Micro 30, 467–474) are exploited to generate synthetic sequence analogs using conventional methods.

In a particular embodiment, the phycobiliprotein domain is characterizable as an α or β subunit, based on its sequence similarity to natural α and β phycobiliprotein subunits. The selection of α or β phycobiliprotein domains may yield different results, affecting the displayed domain, the carrier protein, or both, and such differences guide the selection of the carrier phycobiliprotein subunit. For example, the phycocyanin a subunit and the β-L11-α subunit-fusion are preferred when the foreign protein is displayed on the N-terminus of the carrier protein because of the higher yield and the better spectroscopic properties of the resulting fusion protein. For display on the C-terminus, phycocyanin β subunit and the α-L11-β subunit fusion are better suited because the phycocyanin a subunit is sensitive to extension on its C-terminus (usually leading to incomplete bilin addition and in some instances partial unfolding of the protein).

In a particular embodiment, the phycobiliprotein domain confers fluorescence on the fusion protein, preferably providing fluorescence quantum yield and molar extinction coefficients at least 1%, preferably at least 10%, more preferably at least 50%, more preferably at least 75%, more preferably at least 90% and most preferably substantially equivalent to that of a corresponding unfused phycobiliprotein, measured as described herein. Preferred domains provide extinction coefficients of at least 100K, preferably at least 300K, more preferably at least 1M and/or quantum yields of at least 0.25, preferably at least 0.5, more preferably at least 0.6, as described herein. In other preferred aspects of this embodiment, the fluorescence emission spectrum of the fusion protein is substantially equivalent to that of a corresponding unfused phycobiliprotein.

In a particular embodiment, the phycobiliprotein domain of the fusion protein comprises one or more bilins, preferably functional bilins contributing to the visible absorption spectrum of the phycobiliprotein domain and fusion protein, preferably natural bilins. In a particular embodiment, the bilins are covalently coupled to the phycobiliprotein domain, preferably through cysteine thioether linkages, preferably at natural bilin attachment sites. The bilins may be coupled to the phycobiliprotein domain by any mechanism that provides the requisite functionalities, including enzymatic addition. Accordingly, in a particular embodiment, the phycobiliprotein domain of the fusion protein provides a substrate for enzymatic bilin addition, which may provide natural or non-natural bound bilin distribution, preferably a substrate for enzymes which naturally modify a corresponding natural phycobiliprotein.

The displayed domain may be any polypeptide having a requisite functionality and being compatible with that of the phycobiliprotein domain and with assembly of the fusion protein in a functional oligomeric phycobiliprotein. Accordingly, a wide range of displayed domains may be used including domains comprising an affinity tag, an oligomerization moiety, a specific binding moiety and/or a signaling moiety, and including polypeptides which may be coupled to phycobiliproteins by chemical conjugation invention (see, inter alia, U.S. Pat Nos. 4,520,110: 4,542,104; 4,857,474; 5,055,556; 5,707,804; 5,728,528; and 5,869,255).

The displayed domain is preferably of length and sequence sufficient to provide a constrained structure, including at least secondary structure, preferably tertiary structure. In a particular embodiment, the constrained structure is of complexity sufficient to require complex folding and is poorly expressed independent of the fusion protein in active form in conventional expression systems, particularly conventional yeast (e.g. *S. cerevisiae*) and bacterial (e.g. *E. coli*) expression systems. Preferred displayed domains are refractive to expression when expressed independent of the fusion proteins, i.e. substantially not expressed in active form, in conventional expression systems, particularly *E. coli*. The displayed domain may have any spectrophotometric properties compatible with the requisite functionalities of the fusion protein. In a particular embodiment, the displayed domain is substantially transparent to the wavelengths of visible light absorbed by phycobiliproteins, and therefore does not substantially affect the fusion protein and/or oligomeric phycobiliprotein light-harvesting function, and/or is substantially transparent to the wavelength(s) of energy emitted by the phycobiliprotein domain, and therefore is not substantially affected by such energy.

The displayed domain may frequently be displayed on either terminus of the phycobiliprotein domain—important because many proteins preferentially tolerate extension on one of their termini. Preferred expression orientation is readily determined empirically, and in many cases (e.g. for making phycobiliprotein-labeled fluorescent reagents) is advised by published C- and N-terminal GFP fusions. In particular embodiments, display on the N-terminals of a phycobiliprotein β subunit, rather than the α subunit, is more conducive to folding of certain displayed proteins. Use of the subunit-fusion phycocyanins α-L11-β and β-L11-α as the carrier protein may also have certain advantages: the fusion proteins tend to be more stable (see, e.g. Example B, below), and the 1:1 stoichiometry of α and β subunits is ensured.

The fusion proteins may comprise additional components as desired, which may provide modules of functionalities, such as affinity handles, dimer- or oligomerization domains, stabilization domains, specificity domains, signaling domains, etc., apart from any such functionality/ies provided by the displayed domain. For example, for constructs to be used as fluorescent labels, introduction of GCN oligomerization domains enhances both the spectroscopic value (more chromophores) and binding affinity (more sites for intermolecular interaction).

In particular embodiments, the fusion protein comprises a specific binding moiety comprising at least one of a specific binding pair, such as a receptor—ligand pair, e.g. an immunoglobulin antigen-binding domain or antigenic domain, a lectin saccharide-binding domain or glycosylated or glycosylatable domain, an avidin or streptavidin biotin-binding domain or biotinylated or biotinylatable (i.e. providing a substrate for enzymatic biotinylation) domain, etc. In a particular embodiment, the protein comprises a biotinylated or biotinylatable domain, which is preferably biotinylated in the expression system (e.g. cell) selected for expression of the fusion protein. A wide variety of synthetic, semi-synthetic and natural such domains are known in the art, see e.g., Schatz et al. 1993, Bio/Technology 11, 1138–1143; Tatsumi et al., 1996, Anal Biochem 243, 176–180; Samols et al. 1988, J Biol Chem 263, 6461–6464, including homologs in phycobiliprotein producing cyanobacteria, e.g. Gornicki et al. 1993. J Bacteriol 175, 5268–5272; Phung et al., GenBank Accession No. U59235; Nakamura et al. 1998 Nucl Acids Res 26, 63–67. In fact, enzymes sufficient to biotinylate biotinylatable domains have been characterized (e.g. Beckett et al. 1999, Protein Sci 8, 921–929; Buoncristiani et al. 1988, J Biol Chem 263, 1013–1016), permitting in vitro biotinylation (e.g. Li et al., 1992, J Biol Chem 267, 855–863). These biotinylated domains permit especially convenient affinity purification tags (e.g. Cronan 1990, J Biol Chem 265, 10327–10333, Example C, below) and are useful in the many well developed biotin/avidin applications (e.g. Wilchek and Bayer (ed) 1990. Methods Enzymol 184, Academic Press, NY).

In another example, various spacers or flexible linker peptides providing a variety of functionalities, such as a specific endopeptidase recognition and/or cleavage site, an affinity-purification tag, etc., may be used between the displayed and phycobiliprotein domains. For example, when displayed C-terminally to the phycobiliprotein domain, a specific protease recognition and cleavage site can be engineered immediately upstream from the displayed domain so, upon cleavage with the protease, the displayed domain can be cleanly released from the carrier protein. This strategy also works for most proteins displayed on the N-terminus of the carrier protein because the functions of most displayed proteins are not affected by C-terminal extensions several residues long. In situations where such C-terminal extension is highly undesirable, an intein domain (Perler F B, Jan. 1, 2000, Nucleic Acids Res 28, 344–345 "InBase. the Intein Database") can be engineered immediately downstream from the displayed domain. Subsequent excision of intein cleanly releases the displayed domain from the carrier protein.

The linkers may also be used to facilitate display of domains that would otherwise interfere with oligomeric phycobilisome assembly. The length and amino acid sequence requirements of such functionality are readily determined empirically for a given fusion construct. Generally, the linkers are preferably from at least 5, preferably at least 10 residues in length, typically requiring no more than 50, and more often no more than 30 residues. To facilitate an unintrusive orientation (see, e.g. Example A, below) small, flexible residues such as Ala, Gly and Ser are particularly convenient components.

The fusion proteins are incorporated in a functional oligomeric phycobiliprotein. see e.g. Glazer, 1994, Adv Mol Cell Biol 10, 119–149, comprising at least a dimer, preferably an α, β, heterodimer. The oligomers, especially when assembled into higher-order structures such as trimers, hexamers, rods and phycobilisomes, constrain one displayed protein from interacting with another. This is particularly useful in producing proteins whose function is (1) harmful to the cell but (2) dependent on the formation of dimer or multimer. In a particular embodiment. the oligomeric fusion phycobiliproteins are structurally substantially identical to those of corresponding natural phycobiliproteins and preferably provide fluorescence quantum yield and molar extinction coefficients at least 1%, preferably at least 10%, more preferably at least 50%., more preferably at least 75%, more preferably at least 90% and most preferably substantially equivalent to those of corresponding natural phycobiliproteins. In other preferred aspects of this embodiment, the fluorescence emission spectrum of the oligomeric fusion phycobiliproteins is substantially equivalent to those of corresponding natural phycobiliproteins.

Because higher order oligomers (phycobilisomes) can form a complex with the water-splitting oxygen-evolving photosystem II, the surrounding environment of phycobilisomes. unlike virtually all other cellular environments, may be oxidative enough for spontaneous formation of disulfide bonds. Therefore phycobilisome display may be applied to the expression and folding of disulfide bond-containing proteins. Accordingly, the compositions also include functional oligomeric phycobiliproteins comprising the subject fusion proteins and cells comprising such oligomeric phycobiliproteins.

The fusion proteins are expressible in any convenient system compatible with expression of the fusion protein, preferably an empirically optimized host cell, host cell of the most closely related natural phycobiliprotein, or lysate or extract thereof. In a particular embodiment. the fusion protein is expressed at least 1%, preferably at least 10%, more preferably at least 50%. more preferably at least 75%, more preferably at least 90% and most preferably substantially equivalent to that of a corresponding unfused phycobiliprotein domain. A wide variety of expression systems may be used. For example, *Anabaena* cells expressing phycobilisome displayed proteins have normal phenotype and growth rates and can be grown large scale in defined inorganic salt media. Alternatively, cells or protoplasts may be engineered or reconstituted to express requisite lyase subunits (e.g. cpcE and cpcF, e.g. Fairchild et al. 1994, Biol Chem 267, 16146–16154) and/or phycobiliprotein linker proteins (e.g. cpcC, e.g. Swanson et al., 1992, J Bact 174, 2640–2647) under conditions wherein the requisite oligomeric phycobilisome proteins are formed. Reconstituted heterologous cellular systems require either high levels of phycobiliprotein domain expression (sufficient to form dimers; see, Glazer et al., 1973, J. Biol Chem 248, 5679–5685) or the expression of a compatible heterophycobiliprotein domain (to form heterodimers), i.e. simply attempting to express a labeled phycobiliprotein fusion protein with a coexpressed lyase in a hererologous cell is insufficient to form the required oligomeric phycobiliproteins (Schroeder 1997, Phycobiliproteins: Biosynthesis and Applications,UC Berkeley, Dissertation). Alternatively, extracellular or cell free systems, such as lysates, extracts and reconstituted in vitro bilin addition systems may be used (e.g. Arciero et also 1988, J Biol Chem 263; 18343–18349; 18350–18357; 18358–18363). Because phycobiliproteins and phycobilisomes are made at very high levels in the cell, especially under low light intensity, phycobiliprotein display also helps to increase the yield of the displayed protein.

The subject methods include methods for making a functional displayed domain, the method comprising the step of combining a polypeptide comprising a displayed domain and a phycobiliprotein domain with a phycobiliprotein subunit under conditions to form a subject fusion protein. In particular embodiments, the methods further comprise prior to the combining step, the step of making the polypeptide by expressing a nucleic acid encoding the polypeptide: and/or after the combining step, the step of separating the functional displayed domain from the functional phycobiliprotein domain. The methods steps may occur intracellularly, e.g. in a cell which is or is a progeny of a natural cell which naturally makes functional phycobiliprotein.

Our extensive studies on phycobiliprotein subunit fusion constructs demonstrate the versatility of phycobilisome display. In fact, our display concept may be practiced with other macromolecules, such as ribosomes, and such macromolecular complex display can also help in posttranslational modification of proteins. For example, proteins displayed on 80S ribosomes in eukaryotic cytosol can undergo different posttranslational modifications than proteins displayed on 70S ribosomes in the mitochondria and chloroplasts. Similarly, proteins displayed on different sides of the ER are also subjected to different modifications.

EXAMPLES AND DETAILED EXPERIMENTAL PROTOCOLS

Example A

Expression and characterization of recombinant phycobiliprotein fusion proteins. We describe here the expression of genes engineered to encode *Anabaena* sp. PCC7120 C-phycocyanin α and β polypeptides bearing a 24-residue N-terminal peptide tag, incorporating a block of six His residues (generally referred to as the "6xHis tag"), in wild-type and mutant cells of the filamentous cyanobacterium *Anabaena* sp. PCC7120. The 6xHis tag allows one-step purification of the recombinant polypeptides by immobilized metal-ion affinity chromatography [IMAC; (8)] away from the wild-type phycobiliproteins. We show here that phycocyanobilin (PCB) is correctly attached to the His-tagged phycocyanin α and β polypeptides and that they fold to yield molecules whose spectroscopic properties correspond to those of wild-type (α and β polypeptides.

Cultures and Strains—*Escherichia coli* strain DH5α (11) grown in LB medium was used in all cloning and expression experiments. Plasmid-encoded resistance to ampicillin or spectinomycin (Sp) was selected at an antibiotic concentration of 100 μg ml$^{-1}$. For overexpression of His-tagged proteins, isopropyl-β-D-thiogalactoside (IPTG) was added to a final concentration of 0.5 mM to exponentially growing cultures to derepress the trc promoter. Induced cultures were usually grown with vigorous aeration for 5 hr at 30° C. to reduce formation of inclusion bodies. Induced cells were pelleted and stored at −20° C. until use.

*Anabaena* sp. strain PCC7120 and its derivative strains were grown at 30° C. on modified AA minimal medium plus nitrate (12) under medium (75 μE m$^{-2}$ s$^{-1}$) to high (200 μE m$^{-2}$ s$^{-1}$) light intensity provided by cool-white fluorescent bulbs. *Anabaena* cultures overexpressing His-tagged phycocyanin subunits were grown in half-strength AA plus nitrate medium (bubbled with 5% $CO_2$ in air, with 2.5 mM HEPES pH 9.0 buffer to maintain pH) to late-exponential phase before addition of IPTG to 0.5 mM. The cultures were induced for 2 to 3 days before cells were harvested and stored at −20° C. Triparental mating to introduce free-replicating plasmids into *Anabaena* cells from *E. coli* was performed essentially as described (13). Strains bearing the plasmid-borne aadA gene, encoding resistance to streptomycin (Sm) and to Sp, were selected at 1 μg ml$^{-1}$ Sm plus 10 μg ml$^{-1}$ Sp on agar-solidified medium and at 20 μg ml$^{-1}$ Sp alone in liquid medium. Mutant strains B646, B64328, and B64407 generated by transposon insertion (7) were selected with neomycin sulfate (Nm) at 200 μg ml$^{-1}$ on solid medium and 10 μg ml$^{-1}$ in liquid medium.

Cloning of *Anabaena* sp. PCC7120 C-Phycocyanin α and β subunits—Standard procedures were used for most molecular biological manipulations (14). Genomic DNA was isolated from *Anabaena* sp. PCC 7120 as described (15). The cpcA and cpcB genes encoding the α and β subunits of phycocyanin, respectively, were amplified for genomic DNA by the polymerase chain reaction (PCR; 16). The 0.5-kb PCR fragment was digested with the restriction enzymes NdeI and HindIII, and cloned into NdeI- and HindIII-digested cloning vector pUC19 [(17); GenBank accession No. X02514], giving plasmid pBS185. The 0.5-kb PCR fragment was digested with enzymes NdeI and EcoRI, and cloned into NdeI- and EcoRI-digested pUC19, giving plasmid pBS251. All fragments generated by PCR were sequenced to verify fidelity using the PRISM 373 DNA sequencing system and the dye-terminator cycle-sequencing kit from Applied Biosystems (Foster City, Calif.). DNA and amino-acid sequence analyses were performed with the programs Editbase (Purdue Research Foundation and USDA/ARS) and Lasergene (DNASTAR Inc., Madison, Wis.).

In verifying the sequences of PCR products, two discrepancies were discovered near the end of the published cpcB DNA sequence from the same organism (5). Base number 487 (numbering of the published sequence) is an A instead of a T. This changes the Cys codon (TGC) to a Ser codon (AGC). Another difference is within the tandem CTG repeats shortly before the stop codon. There are four such CTG triplets, rather than only three shown in the published sequence. In addition to sequencing PCR-generated clones, the base changes were also confirmed by sequencing of a restriction fragment containing the entire cpcB gene. The last 36 base pairs of the cpcB gene sequence determined here, encompassing both corrections, encode a 12-amino acid sequence identical to that of another filamentous cyanobacterium, *Mastigocladus laminosus* [(18); GenBank accession No. M75599], and the sequence of the entire CpcB polypeptide aligns much better with those of other C-phycocyanin β subunits (19). The mass of the *Anabaena* sp. PCC7120 β subunit is in excellent agreement with that predicted from the corrected cpcB sequence. A 16.3-kb DNA sequence with the corrected cpcB sequence, the complete sequence of cpcF (see below), and other new information has been deposited into GenBank under accession No. AF178757.

Construction of expression vectors—A family of plasmids was specifically constructed for inducible overexpression of His-tagged polypeptides in both *E. coli* and *Anabaena* sp. PCC7120. Plasmid pBS150v contains the following components: (A) From 0 to 1.3 kb, a portion from pBR322 [(20); GenBank accession No. V01119] that contains the ColE1 oriV for plasmid replication in *E. coli*, the oriT (bom) site for conjugal transfer, and the rop (repressor of primer) gene. Although the first 11 codons of the Rop open reading frame were changed in pBS150v, the modified Rop protein apparently can still form the homodimer four-alpha-helix structure (21), helping to maintain the plasmid at a medium copy number like that of pBR322 (20); (B) From 1.3 to 2.3 kb, most of the C.S4 cassette (22) containing the engineered aadA gene that confers resistance to Sm and Sp; (C) From 2.3 to 4 kb, a portion from the expression vector pPROEX-1 (Life Technologies, Inc.) that contains the lacIq gene coding for the lac repressor, and multiple cloning sites for construction of sequences coding for His-tagged proteins, expression of which is controlled by the trc promoter.

The N-terminal 24 residues contain the 6xHis affinity tag as well as a 7-amino acid recognition and cleavage site for the tobacco etch virus (TEV) protease for removal of the 6xHis tag if so desired (23, 24); and (D) From 4 to 4.6 kb, a portion from the expression vector pMAL-c2 (New England Biolabs, Inc.) that contains the lacZ$^\alpha$ gene for blue/white screening of insert recombinants, and downstream, two strong, bidirectional, ρ-independent transcriptional terminator structures from the *E. coli* rrnB gene (25). The nucleotide sequence of pBS150v has been deposited in GenBank under the accession No. AF177932.

A portion of the plasmid pDU1 (26) coding for a replication protein and a resolvase was inserted in the unique Eco47III site of pBS150v, giving plasmid pBS150. This 3.7-kb fragment, pDU1HC, contains spontaneous mutations that enable autonomous replication of cognate plasmids in higher copy number in *Anabaena* sp. (27). Plasmid pBS152v (sequence also available from GenBank under accession No. AF177933) is similar to pBS150v but sacrifices the lacZ$^\alpha$ gene for more cloning sites like those in pPROEX-1. The pDU1HC$^+$ version, pBS152. was constructed like pBS150. His-tagged constructs were usually made using the small, "v" versions of the plasmids and then converted to the larger, pDU1HC-containing form. When induced, the trc promoter initiates very strong transcription in both *E. coli* and *Anabaena*. While very tightly controlled in *E. coli*, the trc promoter is poorly repressed in *Anabaena* sp. partially due to the atypical promoter and the presence of some codons unfavorable to *Anabaena* sp. in the lacI$^q$ gene, leading to a relatively high level of constitutive expression of the 6xHis-tagged proteins. Preliminary Western analyses showed only about three-fold increase in production of His-tagged proteins in *Anabaena* cultures upon induction with IPTG.

Isolation of phycobilisomes—Phycobilisome (PBS) preparations were characterized on discontinuous sucrose density gradients as described (28), with minor modifications. Frozen or freshly harvested *Anabaena* cells were used with no obvious difference in results. Na/K-PO$_4$ buffer (0.75M; 1:1 ratio of Na-PO$_4$ and K-PO$_4$. pH 7.5) containing 1 mM each of NaN$_3$ and ethylenediamine tetraacetate (EDTA), was used. Individual PBS, rod, and hexamer fractions collected from the sucrose gradients were dialyzed extensively against buffer 0 (20 mM Tris-HCl pH 8.0, 50 mM NaCl, 50 mM KCl) to eliminate sucrose, phosphate, azide, and EDTA before isolation of His-tagged phycobiliproteins on a Ni$^{2+}$-NTA column (see below). Similarly, for isolation of intact His-tagged PBS on Ni$^{2+}$-NTA, the PBS fraction was dialyzed against 0.75 M phosphate buffer, pH 7.5 (without EDTA and azide) prior to loading on a Ni$^{2+}$-NTA column (see below).

To isolate PBS containing His-tagged phycocyanin subunits, the PBS preparation in 0.75 M phosphate was loaded on 1 ml of Ni$^{2+}$-NTA resin pre-equilibrated with 0.75 M phosphate buffer. The high concentration of phosphate, along with possibly lesser steric availability of the 6xHis tags of phycocyanin subunits incorporated within PBS, significantly decreased the rate of binding of PBS to the Ni$^{2+}$-NTA resin. Several passages of the same sample through the column were needed to get adequate binding. The resin was then washed with 20 column volumes of 0.75 M phosphate buffer plus 30 mM imidazole. PBS bound on resin were eluted with 0.75 M phosphate buffer plus 200 mM imidazole. The eluate was immediately dialyzed against 0.75 M phosphate buffer to remove imidazole.

Isolation of His-tagged Proteins by Immobilized Metal Affinity Chromatography—Cell pellets were thawed and resuspended in 10 to 20 volumes of cold (0–4° C.) buffer 0. Phenylmethylsulfonyl fluoride (PMSF) and β-mercaptoethanol were added to give final concentrations of 1 mM and 10 mM, respectively, immediately before breakage of cells by passage through a French press cell, three times at 18,000 p.s.i. Cellular debris was then removed by centrifugation at 4° C. in an angled rotor at 30,000×g for 20 min (preparations from *E. coli*) or at 130,600×g for 1 hr (preparations from *Anabaena* sp.). The supernatant was loaded on a column of 1 to 3 ml of Ni$^{2+}$-NTA resin pre-equilibrated with buffer 0. The resin was then washed consecutively with ten column volumes each of cold buffer A1 (20 mM Tris-HCl pH 8.0. 50 mM NaCl, 50 mM KCl, 20 mM imidazole, 5% v/v glycerol), buffer B (20 MM Tris-HCl pH 8.0, 500 mM NaCl, 500 mM KCl), and buffer A2 (20 mM Tris-HCl pH 8.0, 50 mM NaCl, 50 mM KCl, 30 mM imidazole). His-tagged proteins were eluted from the resin with buffer C (20 mM Tris-HCl pH 8.0, 50 mM NaCl, 50 mM KCl, 200 mM imidazole). The eluate was immediately dialyzed against 50 mM Tris-HCl pH 8.0, 50 mM NaCl, 50 mM KCl. 1 mM DTT, to remove imidazole which at high concentrations is slightly denaturing to proteins. Recombinant His-tagged phycocyanin isolated in this manner consisted mostly of αβ heterodimers. A crude estimate of the yield of His-tagged phycocyanin was calculated from the amount of phycobiliprotein (expressed in units of $A_{620\ nm}$ ml) eluted with buffer C vs. the total amount of phycobiliprotein applied to the Ni$^{2+}$-NTA resin.

Size Exclusion Chromatography-High Performance Liquid Chromatography—Although IMAC-purified and dialyzed samples (see above) could be used with no obvious effect on the results, proteins to be analyzed by SEC-HPLC were generally dialyzed again in 50 mM Na—PO$_4$ pH 7.0, 50 mM NaCl, 0.5 mM DTT. SEC-HPLC separations were performed with a Waters 600 pump and line detection achieved with a Waters 991 photodiode array detector (Waters Associates, Milford, Mass.). A mobile phase of 50 mM Na—PO$_4$ pH 7.0 was flowed at 0.8 ml min$^{-1}$ through Bio-Sil 250 (Bio-Rad Laboratories, Hercules, Calif.) guard column (80×7.8 mm) and column (300×7.8 mm) maintained at 25° C. For analytical separations, 50 to 200 µg of phycocyanin was loaded [based on absorbance at the peak near 621 nm and using a molar extinction coefficient of 290,000 M$^{-1}$ cm$^{-1}$ per monomer (29)]. Molecular size calibration utilized bovine gamma globulin, 158 kDa; chicken ovalbumin, 44 kDa; horse myoglobin, 17 kDa; vitamin B12, 1.35 kDa (Bio-Rad gel filtration standards). The void volume was determined with blue dextran, 2000 kDa (Pharmacia Biotech, Piscataway, N.J.). Preparative separations were performed with loads of 0.5 to 1 mg phycocyanin.

Analytical Ultracentrifugation—Measurements were performed on a Beckman XLA centrifuge using an An-60Ti rotor maintained at 20° C. and 20,000 rpm. Affinity-purified samples were run at a concentration of 0.5 mg ml$^{-1}$ in dialysis buffer. Data were fit to a two component regression (which was superior to a single-component fit) and the molecular weights determined with the HID4000 software.

SDS-Polyacrylamide Gel Electrophoresis—Proteins were precipitated with 10% (w/v) trichloroacetic acid, washed once with ice-cold water, and resolubilized in SDS loading buffer [2% sodium dodecyl sulfate, 50 mM Tris-HCl, pH 6.8, 100 mM DTT, 0.1% Bromphenol Blue. and 10% v/v glycerol; (13)]. SDS-PAGE (30) was performed using 10% acrylamide stacking, and 14% separating gels, with monomer/bis ratio of 37.5:1. Bilin-bearing polypeptides were visualized as fluorescent bands by UV (>312 nm) illumination after staining with 10 mM zinc acetate (31). Polypeptides were also visualized by staining with Coomassie Brilliant Blue. Protein molecular weight standards were purchased from Bio-Rad Laboratories.

Absorbance and Fluorescence Spectrometry—Absorbance spectra were acquired on a computer-controlled, dual-beam λ6 UV/V is spectrophotometer (Perkin-Elmer Corp., Norwalk. Conn.). Absorbance of *Anabaena* cell suspensions was measured from 400 to 750 nm with a light beam passing through the frosted side of a 1-cm light path square cuvette. Fluorescence measurements were performed, on samples with a maximal absorbance of less than 0.07 to minimize the inner-filter effect, with a Perkin-Elmer MPF-44B fluorimeter coupled with an I/O board to a Macintosh computer for digitization and storage of data. Excitation and emission slits were set at 5 or 6 nm for all measurements. Excitation spectra were measured with emission observed at a wavelength 10 nm to the red of the sample's fluorescence emission maximum.

Fluorescence quantum yield measurements, for samples isolated from SEC-HPLC, were made relative to cresyl violet (in ethanol, $\Phi_f$=0.59; Eastman Kodak Co., Rochester, N.Y.) using the K2 multifrequency phase and modulation fluorimeter (ISS, Champaign, Ill.) with excitation and emission slits set at 8 nm. All samples were diluted to peak absorbance between 0.01 and 0.05, excited at 570 nm and emission acquired from 575 to 800 nm. These emission spectra were then instrument-corrected, converted to wavenumber scale, and bandpass corrected by multiplying emission intensity at each wavelength by the square of the respective wavelength (32). The resulting spectra were integrated and quantum yields calculated according to previously described equations (33).

Molar extinction coefficients were determined according to previously established methods (34). In brief, absorbance spectra of samples isolated as trimers (unless otherwise noted) from SEC-HPLC were measured. These samples, having peak absorbance between 0.9 and 1.2. were diluted 10× with 8 M urea, pH 1.9 containing 10 mM DTT. The absorbance was measured at 660 nm for these denatured samples, and molar extinction coefficients were calculated for the original native samples from the known value of 35,400 $M^{-1}$ $cm^{-1}$ (at 660 nm) for each peptide-bound PCB in acid urea (35). Calculations assumed a stoichiometry of one PCB per α subunit and two PCBs per β subunit. Molar extinction coefficient of each peptide-bound PCB at 280 nm was measured using trimeric phycocyanins purified from SEC-HPLC. Samples in 50 mM Na-PO₄ pH 7.0, with peak absorbance between 1.0 and 1.5 at 620 nm, were denatured with 9 M urea to give final 8 M urea, pH 2.0. The extinction coefficient of a protein-bound PCB at 660 nm was identical to the value mentioned above, while that at 280 nm was calculated by subtracting, contributions from Tyr [$\epsilon_{280\ nm}$=1,370 $M^{-1}$; (36)] and Trp [$\epsilon_{280\ nm}$=5,500 $M^{-1}$ $cm^{-1}$: (37)] residues.

Mass Spectrometry—For electrospray mass spectrometry, purified proteins (0.5 to 1 mg) were dialyzed extensively against 10 mM ammonium acetate prior to lyophilization. Proteins redissolved in 50% acetonitrile in 0.2% aqueous formic acid were analyzed with a VG Bio-Q mass spectrometer as described (38). Mass spectral analysis of different phycobiliprotein polypeptides, as well as of some other proteins expressed in *Anabaena* sp., showed quantitative posttranslational removal of the N-terminal Met in *Anabaena* sp. PCC7120. For this reason. amino acid residue numbering starts from the residue after the initial Met, and follows that used for numbering of bilin-linked residues in crystallographic studies of the highly homologous phycocyanin from *Mastigocladus laminosus* (39). However, our examination of phycobiliproteins from other cyanobacteria, as well as amino acid sequence data published big others (40, 41), showed that such posttranslational processing is not universal to cyanobacteria.

Molecular modeling of His-tagged C-phycocyanin—The crystal structure of C-phycocyanin from the cyanobacterium *Fremyella diplosiphon* has been solved at 1.75 Å, resolution (42). The structural data for that phycocyanin, which is highly homologous to that of *Anabaena* sp. PCC7120, were used to build a molecular model of the *Anabaena* C-phycocyanin with the 24-amino acid N-terminal extension on the α subunit. Examination of the C-phycocyanin hexamer structure revealed a groove lying on the β face between β subunits. In order to present a reasonable graphical representation of the HTα:β model, we chose to lead the 24-amino acid extension from inside to outside of the ring structure of phycocynin trimer through this surface groove. Although structural data supporting this choice is lacking, our results suggest that this is a plausible placement. Modeling of the 24-residue extension onto the C-phycocyanin hexamer was performed using the published monomer coordinates [(42); PDB accession code: 1cpc]. The 24-residue tag was built onto the N-terminus of the α subunit as follows. First, the coordinates for a well-defined 25-residue peptide (the last one at C-terminus being Met) were excised from the published coordinates of another protein (antibody 48G7; PDB accession code: IGAF). Next, all side chains except for that of the last Met were truncated to Ala (or left as Gly). Using the least-squares superposition of the program LSQ-MAN (43), the C-terminal Met of the 25-mer peptide was overlaid with the N-terminal Met of the α subunit. The tag was then coarsely laid into the above-mentioned groove using the torsion commands of the program O (44), and the side chains mutated again to conform with sequence of the 24-residue tag of HTα. Again, using only the torsion commands, phi, psi, and chi angles on the 24-residue tag were manipulated so as to conform to the following constraints: (a) all non-bonded contacts involving tag-to-tag and tag-to-phycocyanin atoms must be in excess of 2.5 Å; (b) large part of the tag must lay more or less in the β-face groove; and (c) the six His residues must place externally to the hexamer so as to be solvent-accessible. The model was then subjected to 200 rounds of Powell energy minimization using the program XPLOR (45, 46), during which all of the original C-phycocyanin atoms were constrained from movement. This resulted in the torsion angles and non-bonded contacts of the 24-residue tag approaching canonical values. Quality of the model with respect to phi/psi angles was verified using the program PROCHECK (47). The Ramachandran plot showed that the modeled tag contained no disallowed phi or psi angles. To build trimers, symmetry operators were applied to the HTα:β monomer model using program O. The hexamer model was built by adding the tag coordinates to the second α subunit coordinates of the 1cpc structure and then applying the symmetry operators.

Nomenclature—A His-tagged protein preparation purified by IMAC may contain more than one protein species. For example, both the apoprotein and holoprotein version of a His-tagged phycocyanin subunit may be present. Consequently, we refer to such a preparation by a nomenclature which specifies the organism in which it is being expressed (i.e., *Anabaena* sp. or *E. coli*), and the number of the pBS plasmid which contains the gene encoding the recombinant subunit. Thus, when His-tagged phycocyanin α subunit is expressed in *Anabaena* sp. PCC7120 bearing the plasmid pBS168, the fraction purified by IMAC is designated An168. A fully characterized fraction, shown to consist of a single species, for example, pure His-tagged phycocyanin α subunit, is designated HTα. A mutant polypeptide, for example, a His-tagged *Anabaena* sp. PCC7120 phycocyanin α subunit with a Thr residue in place of an Ala residue at position 12, is designated HTα$^{A12T}$. The absence or presence of the bilin chromophores is indicated by the prefixes "apo" and "holo", respectively. A His-tagged α subunit with native β subunit non-covalently associated is designated HTα:β.

Table 1 summarizes the properties of each of the *Anabaena* sp. PCC7120 wild-type and derivative strains and of expression vectors carried by these strains used for the production of His-tagged C-phycocyanin normal and mutant α and β subunits.

Expression of His-Tagged C-Phycocyanin α Subunit in Wild-Type *Anabaena* sp.—The 0.5-kb NdeI-cpcA-HindIII fragment from pBS185, encoding the wild-type phycocyanin α subunit, was cloned into pBS150, giving plasmid pBS168 encoding the α subunit with a 24-residue N-terminal extension. Cultures of *Anabaena* sp. PCC7120(pBS168) expressing 6xHis-tagged phycocyanin α subunit were very similar to wild-type cultures grown under identical conditions with respect to the relative amounts of phycobiliproteins and chlorophyll, and showed no apparent negative phenotypic characteristics.

Isolation and characterization of HTα—When cell lysate supernatant from *Anabaena* sp. PCC7120(pBS168) was passed through a Ni$^{2+}$-NTA affinity column, some 30 to 40% of the cell phycobiliprotein (as estimated from $A_{m\alpha}$ at 620 nm) was retained on the column and then eluted with imidazole, a His-tag competitor. SDS-PAGE analysis of the His-tagged protein fraction showed two bands of 21.9 kDa and 19.5 kDa, corresponding to the calculated molecular weights of His-tagged C-phycocyanin α and native β subunits, respectively. Upon Zn$^{2+}$-staining, both bands showed red fluorescence with near-UV excitation, indicating that each carried covalently linked phycocyanobilin. Identification of the two polypeptides was confirmed by mass spectrometry, which showed two components of 20,791.4±2.3 (holo-HTα minus the N-terminal Met) and 19,441±1.3 (holo-β minus the N-terminal Met) in a 1:1 ratio. These mass values confirm the presence of one PCB on HTα and two PCBs on the β subunit. No other signiticanii peaks, especially that corresponding to an apo-HTα, were present in the mass spectrum. These data indicate that the protein purified by IMAC, An168, is phycocyanin holo-HTα:holo-β.

The assembly forms of phycocyanin holo-HTα:holo-β and their apparent molecular weights were determined by analytical SEC-HPLC. As shown in Table 2, three components were present under our particular chromatographic conditions, a monomer (calculated mass 40.5 kDa) at 49.2 kDa, a trimer (calculated mass 121.5 kDa) at 145.3 kDa, and a hexamer (calculated mass 243 kDa). Over 90% of the protein was trimeric, (HTα:β)$_3$, the major assembly state observed under these conditions for native PC isolated from wild-type *Anabaena* sp. PCC7120. The SEC-HPLC data were corroborated by analytical ultracentrifugation, where most of the HTα:β was found to have a mass of 125.9 kDa, and the balance a mass of 34.8 kDa (Table 2). All three fractions from SEC-HPLC were shown by SDS-PAGE to contain holo-HTα and holo-β in a ratio of 1:1. Thus, the An168 His-tagged protein preparation purified by IMAC consists of HTα:β, and displays aggregation behavior typical of native PC under similar in vitro conditions.

(HTα:β)$_3$ isolated by SEC-HPLC had a $\lambda_{max}$ of 621 nm at protein concentrations >0.5 mg ml$^{-1}$, and gave spectra with blue-shifted maxima (to as low as 615 nm) upon dilution (Table 3). This is consistent with the blue shift in $\lambda_{max}$ of wild-type phycocyanin when higher order assemblies dissociate to monomers as the protein concentration is lowered (48). Interestingly. at high protein concentrations, HTα:β displays a $\lambda_{max}$ slightly red-shifted relative to that of native PC measured at similar concentrations. The $\epsilon_M$ of (HTα:β)$_3$ was determined to be 9.21×10$^5$ M$^{-1}$ cm$^{-1}$ at 621 nm, similar to values observed for native phycocyanin from *Anabaena* sp. and other cyanobacteria [Table 3; (49)]. The excitation spectrum for 650 nm emission coincided nearly perfectly with the absorbance spectrum, indicating that the HTα:β preparation behaved as a single species with respect to spectroscopic properties. The λ was at 642 nm (with 560 nm excitation) with a $\Phi_F$ of 0.22, similar to a value of 0.27 measured for native *Anabaena* PC (Table 3). In summary, the spectroscopic characteristics of HTα:β are virtually identical to those of native *Anabaena* sp. PCC7120 C-phycocyanin.

Incorporation of HTα into Phycobilisomes—Since holo-HTα:holo-β represents between 30 and 40% of the total phycobiliprotein in *Anabaena* sp. PCC7120(pBS168), it appeared likely that holo-HTα is effectively incorporated into phycobilisomes. This possibility was examined bit analyzing phycobilisomes and their partial dissociation products for the presence of holo-HTα. Compared to the wild-type *Anabaena* sp. PCC7120 phycobilisome preparation, in the *Anabaena* sp. PCC7120(pBS168) preparation a lower percentage of the total phycobiliproteins was found in the phycobilisome fraction, while more was found in the rod substructure and the hexamer fractions. This indicates that the phycobilisomes of the strain expressing holo-HTα are less stable under the conditions used for phycobilisome preparation. SDS-PAGE analysis showed that holo-HTα was present in all three fractions.

*Anabaena* sp. PCC7120(pBS168) phycobilisomes loaded on a Ni$^{2+}$-NTA column (in the 0.75M Na/K-PO$_4$ pH 7.5 buffer needed to maintain phycobilisome integrity, see "Materials and Methods"), bound to the column, although the binding capacity of the column under these conditions appeared low. The His-tagged phycobilisomes were eluted at high imidazole concentration. After removal of imidazole by dialysis, the SDS-PAGE polypeptide profile and spectroscopic properties of this phycobilisome fraction were very similar to that of the starting phycobilisome preparation. These results show that the 6xHis tags of the HTα subunits incorporated into phycobilisomes are relatively exposed, available for interaction with the Ni$^{2+}$-NTA matrix.

Expression of His-Tagged C-Phycocyanin β Subunit in Wild-Type *Anabaena* sp.—The 0.5-kb NdeI-cpcB-EcoRI fragment from pBS251, encoding the wild-type phycocyanin β subunit. was cloned into pBS150, giving plasmid pBS262 encoding the β subunit with the 24-residue N-terminal extension. Cultures of *Anabaena* sp. PCC7120 (pBS262) expressing HTβ were phenotypically very similar to those of *Anabaena* sp. PCC7120(pBS168) expressing HTα, except for a slightly yellowish appearance. Their whole-cell absorbance spectra showed a small decrease in the amount of phycobiliprotein per cell relative to chlorophyll.

The yield of the His-tagged phycobiliprotein fraction from *Anabaena* sp. PCC7120(pBS262) was 16–18% of the total phycobiliprotein in the cell lysate, substantially lower than the 30–40% in the corresponding fraction from *Anabaena* sp. PCC7120(pBS168) expressing HTα (see above). Analysis of the His-tagged phycobiliprotein preparation, An262, by SDS-PAGE showed the presence of holo-HTβ and holo-α in equal amounts. Mass spectral analysis showed that the two subunits carried the normal amounts of PCB, i.e., one PCB per α and two per HTβ subunit, and no apo-polypeptides were present.

In analytical SEC-HPLC, the α:HTβ holoprotein preparation isolated by IMAC was primarily trimeric (calculated mass 121.5 kDa) at 136.9 kDa. The shoulder/tail of that peak, constituting less than 5% of the total His-tagged protein loaded, could be attributed to monomers (calculated mass 40.5 kDa) at 62.4 kDa (Table 2). Both fractions were shown by SDS-PAGE to contain holo-α and holo-HTβ in a molar ratio of 1:1. In contrast to native PC and the HTα:β holoprotein, the hexamer component was not observed for the α:HTβ holoprotein. Analytical ultracentrifugation data were consistent with two components observed in SEC-HPLC: a majority of the α:HTβ holoprotein had a mass of 121.9 kDa, and a small fraction of 43.4 kDa, corresponding closely to the theoretical masses of trimers and monomers, respectively.

The $\lambda_{max}$ of the trimeric α:HTβ holoprotein component lay between 615 and 619 nm depending on protein concentration (Table 3). As observed with HTα:β, $\lambda_{max}$ shifted blue upon dilution. However, at high protein concentration the $\lambda_{max}$ of the α:HTβ holoprotein, like that of native PC, did not exceed 619 nm, in contrast to the $\lambda_{max}$ of 621 nm observed for HTα:β under similar conditions. The $\epsilon_M$ of α:HTβ trimers was found to be $8.88 \times 10^5$ $M^{-1}$ $cm^{-1}$ at 619 (Table 2), a slightly lower value than that observed for HTα:β. The excitation spectrum for 650 nm emission corresponded nearly perfectly to the absorbance spectrum, indicating that the α:HTβ preparation behaved as a single species with respect to spectroscopic properties. The λwas at 642 nm (with 560 nm excitation), with a $\Phi_F$ of 0.23 (Table 2). Thus the spectroscopic characteristics of α:HTβ are virtually identical to those of native *Anabaena* sp. PCC7120 C-phycocyanin and its HTα:β counterpart.

A sucrose density gradient preparation of phycobilisomes from *Anabaena* sp. PCC7120(pBS262) expressing HTβ showed distribution of phycobiliprotein aggregates different from that of the wild-type cells. A much smaller proportion of the phycobiliprotein (25%) sedimented in the phycobilisome fraction, with 40% and 35% in the rod and hexamer fractions, respectively. SDS-PAGE analysis showed that HTβ was present in all three fractions. However, less HTβ (relative to the other phycobiliproteins) was found in phycobilisomes compared to the amount found in the products of phycobilisome dissociation, rods and hexamers, suggesting a reduced stability of phycobilisomes that have incorporated more HTβ subunits. As described above for *Anabaena* sp. PCC7120(pBS168) expressing HTα, His-tagged phycobilisomes could be isolated from the *Anabaena* sp. PCC7120(pBS262) phycobilisome fraction by IMAC, although in a relatively poor yield. The low yield might be due to the smaller number of HTβ subunits present per phycobilisome, a reflection of the smaller amount of holo-HTβ relative to holo-β produced per cell.

Highly purified (HTα:β)$_3$ and (α:HTβ)$_3$ phycocyanins were used to measure the extinction coefficient of peptide-bound PCBs in 8 M urea pH 2.0. Two different preparations were measured for each protein, and four measurements gave very similar values. The molar extinction coefficient for one peptide-bound PCB at 660 nm is very close to the value of 35,400 $M^1$ $cm^{-1}$ (35). Upon subtraction of contributions from Trp and Tyr residues, the extinction coefficient for one peptide-bound PCB at 280 was determined to be $(14.85\pm0.1)\times10^3$ $M^{-1}$ $cm^{-1}$ (Table 3).

Expression of HTα and HTβ in a cpcBAC background— The separate overexpresslion of HTα and HTβ in phycocyanin-minus backgrounds was examined in mutant strain B646 (7). This mutant has a transposon inserted between the promoter and the CpcB open reading frame, which is expected to eliminate transcription of cpcBAC, genes encoding the , and α subunits of phycocyanin and a rod linker polypeptide, respectively (5). Strains B646(pBS168) and B646(pBS262) (see Table 1), generated by introduction of pBS168 and pBS262 into strain B646 by conjugation, were phenotypically indistinguishable from the parent mutant strain. Both phycocyanin-deficient strains grow slowly and produce very low levels of the His-tagged polypeptides.

SDS-PAGE analysis of the His-tagged phycobiliprotein fractions from strain B646(pBS262) showed no α or β subunits of wild-type phycocyanin. However, multiple attempts at purifying the HTα from strain B646(pBS168) yielded fractions containing some native β subunit, presumably resulting from a basal leaky transcription of the cpc-BAC operon.

On SEC-HPLC fractionation, the IMAC-purified proteins from B646(pBS262).An262-BAC, eluted as a single peak of subunit homodimers, i.e., (HTβ)$_2$. Purified native β subunits of C-phycocyanin dimerize at concentrations of 1–10 μM (34, 50). Since mass spectrometry showed that the HTβ subunits produced in this cpcBAC background carried a full complement of PCB, it is evident that bilin addition to phycocyanin β subunit is independent of the presence of the phycocyanin apo- or holo-α subunit. The mass spectral analysis also indicates the presence in HTβ of the posttranslational methylation at the γ-amino group of the Asn$^{72}$ residue normally found in phycocyanin β subunits (51, 52).

Under similar SEC-HPLC conditions IMAC-purified protein preparation from B646(pBS168), An168-BAC, fractionated into three species: trimer, monomer, and subunit. SDS-PAGE analysis of the fractions indicated that the trimer and monomer fractions contained HTα and holo-β in equimolar amounts. The subunit fraction contained only HTα, the majority of which appeared to be apo-HTα based on the relative intensities in the absorption peaks at 280 nm and 618 nm, and from comparison of $Zn^{2+}$- and Coomassie-staining intensities of the An 168-BAC trimer and monomer fractions (HTα:β) run in parallel on the same gel.

Analyses of the His-tagged protein preparations from strains B646(pBS168) and B646(pBS262) indicate that overexpression of HTβ in the cpcBAC background yields a soluble protein where the HTβ subunit is stabilized by homodimer formation. The results also indicate that HTα appears to be unable to form subunit homodimers in the cell, and may require the presence of β subunit that is extremely limited in the cpcBAC background for stabilization. The greatly reduced chromophorylation of HTα protein isolated from this cpcBAC strain may also reflect a possible requirement of subunit dimerization (α:β, α:α, or β:β) prior to covalent attachment of PCB, or misfolding of a significant fraction of apo-HTα in the absence of apo- or holo-β.

The HTα and HTβ subunits isolated from mutant strains B646(pBS168) and B646(pBS262) have absorbance spectra and molar extinction coefficients (Table 3) similar to those reported for renatured α and β subunits of native C-phycocyanin, obtained by chromatographic separation under denaturing conditions (34, 50). Algebraic addition of the HTα and HTβ spectra yielded a spectrum with shape similar to that of monomeric PC but with a blue-shifted maximum at 611 nm, consistent with previous observations (34). Incubation of the HTα and HTβ subunits together overnight at 4° C., followed by fractionation by SEC-HPLC, yielded a trimer fraction with absorbance and fluorescence excitation and emission spectra similar to the corresponding spectra of HTα:β, α:HTβ, and native PC. This indicates that holo-HTα (but not apo-HTα, see below) interacts preferentially with holo-HTβ to form trimers, and His-taggecd holophycocyanin subunits isolated in the absence of their cognate subunit partners can be reconstituted to yield trimers with properties similar to those of native phycocyanin.

Expression of His-tagged phycocyanin subunits in an apophycocyanin α subunit PCB lyase-deficient background—A dimeric lyase, CpcEF encoded by genes cpcE and cpcF, specifically catalyzes the addition of PCB to $Cys^{84}$ of the phycocyanin α subunit (1, 3). We have obtained two mutants through transposon mutagenesis, B64328 with an insertion in the cpcE gene, and B64407 in the cpcF gene. Both mutants had greatly reduced cellular content of normal phycocyanin (7). Expression of His-tagged phycocyanin subunits in the mutant strains provided a simple way of assessing how mutations in each of the two CpcEF lyase subunits affect PCB addition to the phycocyanin to subunit, and how cognate PC proteins behave in the cell.

Expression of HTα in either a cpcE or a cpcF background—To express the HTα polypeptide in either a cpcE or cpcF background, plasmid pBS168 was introduced into both mutants, giving strains B64328(pBS168) and B64407 (pBS168) (see Table 1). The two strains showed the yellowish-green phenotype characteristic of their respective parent mutants. The His-tagged phycobiliprotein fraction from either mutant strain amounted to <5% of the total absorbance of the cell lysate at 607 nm. The His-tagged protein purified from the cpcF strain B64407(pBS168), An168-F, was shown by SDS-PAGE and mass spectral analyses to be apo-HTα:holo-β, with no detectable holo-HTα. In contrast, the An168-E protein contained apo-HTα: holo-β along with a small amount of holo-HTα:holo-β. On SEC-HPLC, apo-HTα:holo-β is seen to form monomers preferentially, in contrast to the preferred trimer formation by holo-HTα:holo-β.

Sucrose density gradient sedimentation patterns of phycobilisome preparation from strains B64328(pBS168) and B64407(pBS168) were very similar to those given by the parental strains B64328 and B64407 (7). In both cases, the phycobilisome fraction consisted largely of the allophycocyanin-containing phycobilisome cores carrying much reduced amounts of rod components (relative to phycobilisomes from wild-type cells). SDS-PAGE analysis showed the presence of apo-HTα in the phycobilisome and rod/hexamer fractions and an amount of phycoerythrocyanin, a distal component of Anabaena phycobilisome rod substructures, greater than that seen in wild-type phycobilisomes (7, 53). The relative amount of apo-HTα was higher in the phycobilisome fraction than in the rod/hexamer fraction, suggesting that apo-HTα assembled into phycobilisomes might be turned over more slowly in the cell.

The finding that apo-HTα:holo-β assembles into phycobilisomes is consistent with earlier observations of such incorporation of the phycocyanin apo-α subunit in cpcE and cpcF mutants of the unicellular cyanobacterium Synechococcus sp. PCC7002 (3, 4). We showed previously that the Anabaena sp. PCC7120mutant strains B64328 (cpcE) and B64407 (cpcF) incorporated the phycocyanin apo-α:holo-β into phycobilisomes, and that this "defective" phycocyanin still allowed the assembly into phycobilisomes of the distal phycoerythrocyanin component (7). The experiments reported here extend that observation to phycocyanin apo-HTα:holo-β proteins.

Expression of HTβ in either a cpcE or a cpcF background—To express the HTβ polypeptide in either a cpcE or cpcF background, plasmid pBS262 was introduced into both mutants, giving strains B64328(pBS262) and B64407 (pBS262) (see Table 1). Yield of His-tagged holophycobiliproteins from either mutant strain was low, accounting for <7% of the absorbance of the cell lysate at 607 nm. In contrast to results obtained with the mutant strains expressing HTα (see above), when HTβ was expressed, SDS-PAGE analysis showed that the His-tagged protein preparations contained apo-α and holo-HTβ in a molar ratio of approximately 1:2. SEC-HPLC fractionation showed presence of apo-α:holo-HTβ trimers and monomers, and of $(holo-HTβ)_2$ homodimers. The apo-α:holo-HTβ trimers had spectroscopic properties virtually identical to those of apo-HTα: holo-β trimers described above. Analyses of phycobilisomes and of rod/hexamer fractions showed that some of the holo-HTβ (likely in the form of apo-α:holo-HTβ) was incorporated into both fractions.

Expression of His-tagged mutant phycocyanin subunits—The favorable expression and incorporation of His-tagged wild-type phycocyanin subunits in Anabaena sp. provides a convenient means to perform in vivo and in vitro studies of mutant phycobiliprotein subunits. Here we present two examples.

Expression of $HTα^{A12T}$—One of the cpcA clones generated by PCR using the Taq DNA polymerase was found to have a single G–>A base change leading to an $Ala^{12}$–>Thr mutation in the translated protein. The $Ala^{12}$ residue is conserved in all sequenced phycocyanin α subunits (19). The crystal structure of phycocyanin predicts that replacement of $Ala^{12}$ by a residue with a larger side chain would interfere with αβ heterodimer formation by steric hindrance of the interaction of α-$Asp^{13}$ with β-$Tyr^{97}$ (54). We expressed the $HTα^{A12T}$ mutant subunit in wild-type Anabaena sp. PCC7120 to examine this prediction.

The mutant cpcA gene was cloned into pBS150, giving plasmid pBS167. Anabaena sp. PCC7120(pBS167) expressing $HTα^{A12T}$ was phenotypically very similar to strain Anabaena sp. PCC7120(pBS168) (see Table 1). However, the His-tagged protein fraction was obtained in verv poor yield from Anabaena sp. PCC7120(pBS167):<0.15% of the phycobiliproteins in the cell lysate as estimated from $A_{620\,nm}$. While spectroscopically similar to the An 168 His-tagged protein preparation, mass spectral analysis of the An167 His-tagged protein preparation showed two components in similar amounts, with masses corresponding to those of holo-α and holo-$HTα^{A12T}$. These results lead to two conclusions. First, the mutant $HTα^{A12T}$ subunit appeals to have a greatly reduced affinity for the holo-β subunit. Most of the $HTα^{A12T}$ is likely to be present as free subunits in the cell and to be degraded rapidly. $HTα^{A12T}$ also seems to have a low affinity for holo-α, and is consequently stabilized in vivo by the formation of holo-α:holo-$HTα^{A12T}$ dimers. Second, the in vivo covalent attachment of PCB to the phycocyanin α subunit evidently does not require that it form a complex with the β subunit.

Sucrose density gradient preparation of phycobilisomes from strain Anabaena sp. PCC7120(pBS167) gave a banding pattern similar to that from the wild type. The $HTα^{A12T}$ subunit was not detected in phycobilisome and rods fractions, suggesting that $HTα^{A12T}$ was not assembled into the phycobilisomes (although the very low amount of $HTα^{A12T}$ may have evaded detection).

Expression of $HTβ^{S46G,N76D}$—One of the cpcB fragments, PCR-amplified using the Taq DNA polymerase, contained two mutations: both an A–>G change, in bases number 139 and 229, respectively, of the published sequence (5). The changes resulted in the replacement of residue $Ser^{46}$ with Gly, and of residue $Asn^{76}$ with Asp in the CpcB protein.

*Anabaena* sp. PCC7120(pBS162) expressing the HTβ$^{S46G,N76D}$ mutant PC subunit was phenotypically identical to the one expressing His-tagged wild-type β subunit. The HTβ$^{S46G, N76D}$ mutant protein behaved the same way as the His-tagged wild-type counterpart in all aspects tested (yield, assembly states in vitro, assembly into phycobilisome in vivo, etc.) except that the purified protein, An162, had an absorption maximum at 610 nm, about 8-nm blue-shifted compared to that of the An262 protein. Fluorescence emission maximum of the An162 protein, however, was still at 642 nm.

Ser$^{46}$ of the phycocyanin β subunit, situated in the coil region connecting helices A and B (39, 54), is not in contact with any chromophore. Its non-conserved substitutions include Gly in some phycobiliprotein subunits. It therefore may be assumed that the Ser$^{46}$–>Gly change would not have obvious effects on the protein. The Asn$^{76}$ residue, on the other hand, is highly conserved among multi-chromophore β subunits of phycobiliproteins (19), and its sidechain is in contact with ring D of the α-84 PCB chromophore of PC trimers, possibly involved in maintaining its stretched confirmation in trimer aggregates (55). The neighboring Arg$^{77}$ residue. also highly conserved, forms a hydrogen bond with the propionic acid substituent of ring B of the β-84 PCB (54, 55). In the mutant protein, replacement of Asn$^{76}$ by Asp$^{76}$ sidechain may interfere with that hydrogen bonding, thereby affecting absorbance of β-84 PCB. A reduction of absorbance of β-84 PCB would shift the $\lambda_{max}$ of the cognate phycocyanin to the blue (50).

Molecular modeling of His-tagged C-phycocyanin— Based on crystallographic data obtained from the cyanobacterium *Fremyella diplosiphon* C-phycocyanin (42) that is highly homologous to that of *Anabaena* sp. PCC7120, a molecular model was built for the *Anabaena* sp. PCC7120 C-phycocyanin incorporating the 24-residue N-terminal extension. In this particular model, the N-terminal extension can be led from inside to outside of the ring structure of the phycocyanin trimer, through a groove between β subunits on the β side of the trimer. This allows unhindered α face-to-α face stacking of two trimers to form a hexamer. The 24-residue N-terminal tag, occupying only the groove space in the β faces, also does not appear to interfere with stacking of hexamers on β faces to form rods of the phycobilisome. The first N-terminal 13 of the 24 residues of the tag, that include the six His residues, are completely exposed outside of the rod surface, consistent with the observed affinity purification of phycobilisomes by IMAC (as described above).

In summary, methodology developed in this study allows (a) high level expression of holo-HTα and holo-HTβ in *Anabaena* sp. PCC7120 and a variety of its mutant derivatives; (b) facile affinity purification of the His-tagged polypeptides and of complexes into which they are incorporated, including intact phycobilisomes; (c) study of in vivo assembly and bilin addition: and (d) analysis of site-specific mutants of C-phycocyanin. It is evident that the approaches described here are immediately generalizable to other *Anabaena* phycobiliproteins, such as allophycocyanin and phycoerythrocyanin (3, 7, 29).

With appropriate choice of organism, these approaches can be applied to the expression and study of other phycobiliproteins including phycoerythrins. Finally, the studies described here provide for the design and expression of diverse fusion proteins in *Anabaena* sp. with important outcomes for the successful production of modular fluorescent phycobiliprotein tags and for the exploration of heterologous protein folding in cyanobacteria (9, 10).

Example B

Recombinant phycobiliprotein fusion proteins with oligomerization and biospecfic recognition domains. Here we describe the design and expression of more complex recombinant phycobiliprotein constructs which incorporate oligomerization and biospecific recognition domains and in some of which the α and β subunits are covalently bridged. Materials and methods essentially as described in Example A are not restated.

Assays of protein binding to streptavidin—Western hybridization was carried out essentially as described (14). Proteins separated on SDS-PAGE were transferred to polyvinylidene difluoride (PVDF) membrane (Immobilon; Millipore Corp., Bedford, Mass.) using a mini Trans-Blot cell (BioRad Laboratories). Electrophoretic blotting was carried out in ice-cooled transfer buffer for 1 hr at 100 V. The PVDF membrane was then blocked with 3% bovine serum albumin in PBS buffer (115 mM NaCl, 4 mM KH$_2$PO$_4$, 16 mM Na$_2$HPO$_4$, pH 7.4) plus 0.5% Tween-20 (Sigma Chemical Co.). Binding of membrane-bound proteins to streptavicdin was assayed by incubating the membrane at 25° C. for 1 hr in PBS buffer plus 0.1% Tween-20 and 1:5000-diluted streptavidin-alkaline phosphatase conjugate (Prozyme Inc., San Leandro, Calif.). Alkaline phosphatase-mediated color development on the membrane using chromogenic substrates 5-bromo-4-chloro-3-indolyl phosphate (BCIP) and nitro blue tetrazolium (NBT) was carried out as described (14) except that 200 mM Tris-HCl pH 8.8 was used as the developing buffer.

Alternatively, streptavidin-coated agarose beads were used to test binding of Strep2-tagged phycocyanin. As has been described (56), beads coated with recombinant core streptavidin (Biometra Inc., Tampa, Fla.) gave better results than those coated with natural streptavidin (Sigma Chemical Co. or Prozyme Inc.). Streptavidin-coated beads were incubated at 4° C. for about 20 min with excess amount of purified Strep2-tagged phycocyanin, washed twice with buffer W (100 mM Tris-HCl pH 8.0, 1 mM EDTA), and visualized by fluorescence. Phycocyanin-labeled beads were observed either in batch with ultraviolet (>312 nm) excitation of fluorescence viewed through a 550 nm long-pass filter, or under an epifluorescence microscope (the BH-2 system from Olympus America Inc., Lake Success, N.Y.) with excitation light through a 450–480 nm band-pass filter and emission observed through a 515 nm long-pass filter.

Construction of modular cloning vectors for protein expression—A series of cloning anal expression vectors was designed and constructed for expression of fusion proteins with different functional domains and tags on the N-terminus. To facilitate shuffling of the functional domains to produce desired combinations, DNA cassettes coding for these domains were designed as exchangeable modules. Care was taken in the design to ensure that only optimal codons (in respect to *E. coli* and *Anabaena* sp. PCC7120) were used, and that no restriction sites (for 6-bp cutters) were present in the core sequences, except for designed-in signature sites.

The expression vector pBS150v [Example A; GenBank Accession number AF177932] was used as a template in the engineering of functional domains. Generally, a pair of designed oligonucleotide primers was used to run inverse PCR, producing a new plasmid in which the sequence from bp 3892 to 3938 (encoding the 6xHis affinity tag and a spacer) of pBS150v is replaced by a desired functional module.

Replacement with the 56-bp NcoI-BspMII Strep2 module generated plasmid pBS283v (4,644 bp; Table 4). The 10-residue Strep2 tag is able to bind specifically to streptavidin (57).

Replacement with the 146-bp NcoI-AgeI combination module (6xHis plus GCN4-pII) gave plasmid pBS311v (4,734 bp; Table 4), and with the 164-bp combination module (Strep2 plus GCN4-pLI) gave pBS303v (4,752 bp; Table 4). Sequences for the GCN4-pII and GCN4-pLI coiled coil domains were modified from part of the original *Saccharomyces cerevisiae* GCN4 sequence encoding the leucine zipper domain (58, 59), to conform with the pII sequence (positions a and d are both Ile) or the pLI sequence (positions a and d are Leu and Ile, respectively) (60). A BglII site was engineered into the GCN4-pII coding sequence as a signature site, as was an AsuII site in GCN4-pLI.

With plasmids pBS283, pBS303, and pBS311 in hand, four functional domains, 6xHis, Strep2, GCN4-pII, and GCN4-pLI, are available for further manipulation. Since the different functional domains are modular in design, different cloning and expression plasmids with various combinations of the modules were easily made by simple recombination cloning (Table 4). All resulting plasmids have the modular region end with the second half of either the BVspMII or the AgeI site, encoding a Gly, immediately upstream from the recognition and cleavage sequence for the tobacco etch virus (TEV) endoprotease (Example A, herein, 23, 61). The 7-residue TEV site was retained in all plasmids to act as a spacer between the modular functional domains and the multiple cloning sites into which genes of interest are inserted, and to provide a means of removing the modular functional domains from expressed fusion proteins if so desired. The LacZ$^\alpha$ domain downstream from the TEV site was found to be functional in all cognate plasmids, allowing blue/white screening of inserts in the multicloning region. The multicloning region of these plasmids can be greatly enhanced in lieu of the LacZ$^\alpha$ function by recombination with plasmid pBS152v [(Example A, herein); GenBank Accession number AF177933]. For plasmids encoding phycocyanin subunits, the NdeI-cpcA-HindIII and NdeI-cpcB-EcoRI fragments were taken from plasmids pBS185 and pBS251, respectively (Example A, herein).

Construction of genes encoding phycocyanin subunit-fusion monomers—X-ray crystallographic data obtained from the highly homologous C-phycocyanin from another cyanobacterium *Fremyella diplosiphon* (42) were used to design subunit fusions of the *Anabaena* phycocyanin, see Example A. Straight-line distance between α carbons of the last residue of α subunit and the first residue of β subunit was measured to be 29.5 Å. The distance between the last residue of β subunit and the first residue of a subunit was 32.6 Å. Although the average sum of three chemical bonds' length of a peptide unit is 4.3 Å, the actual straight-line distances between two α carbons were found to range from 3.2 to 3.7 Å among several peptide units measured in the crystal structure. An 11-residue linker was therefore chosen to link the C-terminus of one subunit to the N-terminus of another. The 11-residue linker is sufficiently long to bridge the distance (29.5 to 32.6 Å) between the N- and C-termini of the two subunits, and provides some leeway for bending should this be required for higher-order assembly of the resultant fusion phycocyanins.

One obvious difference between phycocyanins of *Fremyella diplosiphon* and of *Anabaena* sp. PCC7120 is the lack of the initial Met residue in the *Anabaena* subunits as a result of posttranslational modification (Example A, herein). To reduce possible steric interference in the engineered *Anabaena* protein, an Ala was inserted in place of the missing Met at the N-terminus of the subunit following the fusion linker. Since both α and β subunits have an α-helical C-terminal region made up mostly of small hydrophobic residues, Ala was chosen as the first residue in the fusion linker to maintain the local hydrophobic environment. The rest of the linker peptide (L11) was designed for high structural flexibility, and consists mostly of Gly residues and two Ser. Incorporation of the signature site XmnI in the L11 coding sequence not only facilitates characterization of PCR products, but also allows easy construction of fusions of other proteins to the C-terminus of phycocyanin α or β subunits (Example C, herein).

Designed oligonucleotide primers incorporating the L11 linker sequence were used for inverse PCR with template DNA consisting of both pBS185 and pBS251 plasmids (Example A. herein), giving plasmids pBS310 (NdeI-cpcA-L11-cpcB-EcoRI in pUC19) and pBS307 (NdeI-cpcB-L11-cpcA-HindIII). Once sequenced to confirm fidelity, the 1047-bp NdeI-EcoRI fragment of pBS310 was cloned into NdeI- and EcoRI-digested pBS150 (Example A, herein), giving plasmid pBS320 which encodes 6xHis-tagged CpcA-L11-CpcB fusion phycocyanin. In like manner pBS315 was made to encode the 6xHis-tagged CpcB-L11-CpcA fusion protein (Table 4). A PCR-generated spontaneous mutant product, in which 6 bases in the signature XmnI site of the L11 linker sequence had been deleted (giving the L9 linker), was also used in this study (pBS3419; see Table 4).

All other molecular biological manipulations followed standard procedures (14). To ensure sequence fidelity, all DNA fragments that had gone through the PCR process (16) were sequenced using the PRISM 373 DNA sequencing system and the dye-terminator cycle-sequencing kit from Applied Biosystems (Foster City, Calif.). Analyses of DNA and amino-acid sequence data were performed with the programs Editbase (Purdue Research Foundation and USDA/ARS) and Lasergene (DNASTAR Inc., Madison, Wis.).

Nomenclature—A recombinant polypeptide encoded by an expression plasmid is referred to by the plasrnid number, and the His-tagged protein fraction isolated by affinity chromatography is designated by the organism in which the recombinant polypeptide is expressed. For example, a phycocyanin α subunit with both 6xHis and Strep2 tags encoded by plasmid pBS327, expressed in *E. coli* and purified by IMAC is designated Ec327. The purified. characterized protein is then designated as HT-Strep2-α. The same construct expressed in *Anabaena* sp. PCC7120 is designated An327. However, the purified protein is HT-Strep2-α:β, because in *Anabaena* sp. the HT-Strep2-α forms a stable complex with the holophycocyanin β subunit. Phycobiliproteins expressed in *E. coli* are apoproteins (lacking attached phycobilins), whereas those expressed in *Anabaena* sp. are holoproteins, unless otherwise noted.

Design of subunit-fusion phycocyanins—A His-tag at the N-terminus of either an α or a β subunit does not interfere with the folding of these polypeptides into their native structures (Example A, herein). Two possible α/β fusions can be generated with an 11-residue (L-11) linker: HTα-L11-β and HTβ-L11-α. In either construct, one subunit, the α or the b, would have a 24-amino acid extension (including the 6xHis tag) at the N-terminus and a large fusion, linked through L11, at its C-terminus. Both constructs were made to determine the folding and spectroscopic properties of such fusions.

Expression of His-tagged phycocyanin β-α fusion protein in *E. coli*—HTb-L11-α is expressed in *E. coli* as the apoprotein (lacking the three phycocyanobilins). At 37° C., in cultures induced with IPTG for 5 hrs, the fusion protein (Ec315) represented over 5%, of total cellular proteins (>7.5 mg per liter of culture at $10^9$ cells ml$^{-1}$), and at 30° C., in cultures induced with IPTG for 12 hr, some 20% of total cellular proteins. HTβ-L11-α purified by IMAC could be concentrated up to 0.2 mM protein (nearly 8 mg ml$^{-1}$) in 50 mM Tris-HCl pH 8.0, 50 mM NaCl. 50 mM KCl, 1 mM DTT, and 5% glycerol. The yield and solubility were markedly higher than that obtained upon expression of the individual His-tagged phycocyanin subunits, HTα (Ec168) and HTβ (Ec262), in *E.coli* (Example A, herein). With IPTG induction at 30° C., in the latter cases, yields were about 0.1 mg per liter of culture. Upon IPTG induction at 37° C., ~60% of the individually expressed 6xHis-tagged subunits remained in solution while the balance formed inclusion bodies. Thus coexpression of the apo-α and apo-β subunits, inherent in the expression of HTβ-L11-α, evidently promotes folding and concomitant retention of solubility of the recombinant apoprotein.

Expression of His-tagged phycocyanin β-α fusion protein in *Anabaena* sp.—Cultures of *Anabaena* sp. PCC7120 (pBS315) expressing HTβ-L11-α appeared more blue than that of the wild type. Whole-cell absorbance spectra showed a much higher ratio of phycocyanin:chlorophyll a. Despite appearing very healthy, *Anabaena* sp. PCC7120(pBS315) cultures grew about 30% more slowly than the wild type.

When cell lysate supernatant from *Anabaena* sp. PCC7120(pBS315) was passed through a Ni$^{2+}$-NTA affinity column, usually >33% of the total phycobiliproteins (as estimated from $A_{620\ nm}$) was retained on the column and then eluted with imidazole (resultant protein denoted An315). Such high yields are comparable to that of the strain expressing HTα (>30% of $A_{620\ nm}$), and better than that of the strain expressing HTβ (~16%) (Example A, herein).

SDS-PAGE analysis showed that the An315 fraction consisted almost entirely of HTβ-L11-α, along with a small amount (<10%) of native phycocyanin α and β subunits in a ~1:1 ratio. This finding suggests that the fusion construct interacts relatively normally with unmodified phycocyanin in the cell. Such interaction to form higher assemblies is supported by analysis of *Anabaena* sp. PCC7120(pBS315) phycobilisomes, which were indeed found to contain HTβ-L11-α. Much more of the fusion protein was found in the phycobilisome substructures (rods and hexamers/trimers) than in intact phycobilisomes, suggesting that phycobilisomes with a higher content of HTβ-L11-α may be less stable during the preparation procedure. The high amount of HTβ-L11-α relative to native phycobiliproteins in the hexamer/trimer fraction also suggests that the construct is turned over more slowly in the cell. In this context, it is noteworthy that the whole-cell phycobiliprotein fluorescence emission of *Anabaena* sp. PCC7120(pBS315) was twice as high as that of strains expressing His-tagged α or β subunit, and the growth media of this strain often turned blue, the color of phycocyanin.

On SEC-HPLC the An315 preparation fractionated into hexamers and trimers only, with no monomers observed (Table 5). This result parallels those obtained previously with An168 (HTα:β) and An262 (αHTβ), where the α and β subunits are not covalently linked (Example A. herein). The trimer component, (HTβ-L11-α)$_3$, had a $\lambda_{max}$ at 622 nm at >10$^{-6}$ M protein. (H dissociated to monomers at very low protein concentrations, with absorption maxima shifting blue to as low as 615 nm (Table 6), a behavior characteristic of native phycocyanin and of (HTα:β)$_3$ and (αHTβ)$_3$ holoproteins. At high dilution, HTβ-L11-α has an $A_{max}:A_{360\ nm}$ of 6.2, similar to the values observed for monomeric wild-type and His-tagged α:β phycocyanins (Table 6; Example A, herein). The ε for (HTβ-L11-α)$_3$ at >10$^{-6}$ M protein concentration was determined to be 900,000 M$^{-1}$ cm$^{-1}$. The fluorescence emission spectrum for 560 nm excitation of HTβ-L11-α, with λ at 643 nm and a $\Phi_f$ of 0.21, were virtually identical to those of wild-type phycocyanin. The fluorescence excitation spectrum for 655 nm emission corresponded well with the absorbance spectrum (Table 6). The above data show that the HTβ-L11-α fusion phycocyanin has properties virtually identical to those of the wild-type and His-tagged α:β holo-proteins, and indicate that HTβ-L11-α expressed in *Anabaena* sp. has a full complement of bilins, i.e., one PCB per α and two per β subunit.

Mass spectral analysis of the SEC-HPLC trimer fraction, (HTβ-L11α)$_3$, gave a value of 40,993.2±6.8 which corresponds well to the theoretical value (41,118.8 Dal) of the holoprotein HTβ-L11-α with the initial Met residue (131.1 Dal) removed. The mass spectral analysis not only confirms the full posttranslational chromophorylation on both the α and β subunit moieties. but also indicates presence of the posttranslational methylation on the γ-amino group of the Asn$^{72}$ residue of the β subunit domain (51, 52).

Expression of His-tagged phycocyanin α-β fusion protein in *Anabaena* sp.—Like HTβ-L11-α apoprotein (Ec315), HTα-L11-β (Ec320) was expressed in *E. coli* in very high yield in soluble, form. The phenotype and growth rate of cultures of *Anabaena* sp. PCC7120(pBS320) expressing HTα-L11-β were similar to those of strains expressing only His-tagged α or β subunits. The whole-cell absorbance spectrum of *Anabaena* sp. PCC7120(pBS320) was similar to that of the wild type but with a slightly higher and blue-shifted contribution from phycocyanin, and about 50% higher whole-cell phycobiliprotein fluorescence was observed.

Like HTβ-L11-α (An315), HTα-L11-β(An320) was also expressed at very high yield in *Anabaena* sp., often accounting for >32% of total cellular phycobiliproteins. SDS-PAGE showed that affinity-purified An320 proteins were almost entirely HTα-L11-β, with a small amount of copurified native phycocyanin α and β subunits. The ratio of copurified α to β subunits was ≧2, suggesting a reduced affinity of HTα-L11-β for native phycocyanin β subunits.

On SEC-HPLC, the An320 fraction separates into three components: monomers, trimers. and hexamers. It is noteworthy that native C-phycocyanin under the same chromatographic conditions was mainly trimeric with very little monomer, whereas the HTα-L11-β preparation was a ~1:1 mixture of trimers and monomers (Table 5). The theoretical molecular weights from these components are 13, 19, and 9% higher, respectively, than the values observed (Table 5). These discrepancies indicate that the radius of gyration of HTα-L11-β is smaller than that of the wild-type phycocyanin αβ monomer.

At >10$^{-6}$ M protein concentration, the SEC-HPLC trimer and monomer fractions of HTα-L11-β had $\lambda_{max}$ at 608 and 605 nm, respectively. This likely accounts for the blue-shifted phycobiliprotein contribution to the whole-cell absorbance spectrum of *Anabaena* sp. PCC7120(pBS320). Like wild-type phycocyanin, the trimer fraction showed a blue shift in its absorbance spectrum down to 605 nm with decreasing protein concentration, indicative of dissociation of the trimers to monomers. At high dilution, HTα-L11-β has an $A_{max}:A_{360\ nm}$ of 5.2, substantially lower than the value of 6.4 observed for monomeric wild-type and HTα:β phycocyanins (Table 6; Example A).

The unusual characteristics exhibited by the HTα-L11-β protein purified from *Anabaena* sp. were similar to those of apo-HTα:β (Example A, herein). The trimer and monomer SEC fractions of HTα-L11-β were therefore compared to the HTβ-L11-α holo-protein (both fusion proteins have identical amino acid composition). When denatured in acid urea, the trimeric fraction of HTα-L11-β had PCB absorbance about midway between three PCBs per protein (holoprotein) and two PCBs per protein, while the monomeric fraction gave absorbance very close to that of two PCBs per protein. An interpretation of that result is that the α domain of HTα-L11-β fusion protein is not fully chromophorylated. Only about 50% of the trimeric HTα-L11-β proteins had PCB in the α domain, while most monomeric HTα-L11-β proteins had no PCB addition in the a domain. Because of the nearly equal distribution between trimers and monomers, fewer than 30% of the a subunit domains of affinity-purified HTα-L11-β proteins carry bilin. It is noteworthy that apo-HTα:holo-β and apo-α:holo-HTβ proteins also run mostly as monomers on SEC-HPLC, with apparent molecular weights substantially smaller than theoretical calculations (Example A, herein). The fact that most of the HTα-L11-β constructs have an apo-α domain could also explain why more native α than native β phycocyanin subunits were copurified with HTα-L11-β, since the α-Cys$^{84}$ bilin is involved in the α:β interaction and in stable monomer packing (55, 62)

Electrospray mass spectral analysis of the SEC-HPLC monomer fraction of HTα-L11-β gave only one major peak with a value of 40,327.8±5.7, corresponding well with the value of 40,331.7 daltons, obtained by subtracting from 41,118.8 Dal (molecular weight of holo-HTα-L11-β) the values 131.1 (initial Met residue), 57.0 Dal (the C-terminal or the second residue from the N-terminus, Gly), 585.0 (one PCB), and 14.0 (one methyl group). This not only confirms the incomplete bilin addition (likely on the α domain) of HTα-L11-β, but also suggests impaired posttranslational methylation on the γ-amino group of Asn$^{72}$ of the β domain (51, 52). The latter is unexpected because HTβ (Example A, herein) and HTβ-L11-α (see above) purified from *Anabaena* sp. are both fully methylated on β-Asn$^{72}$.

The SEC-HPLC trimer fraction of HTα-L11-β (at >10$^{-6}$M) had a ε of 677,000 M$^{-1}$ cm$^{-1}$. The fluorescence emission spectrum for 560 nm excitation, with λ at 643 nm and a $\Phi_f$ of 0.22, was virtually identical to that of wild-type phycocyanin. The fluorescence excitation spectrum for 655 nm emission corresponded reasonably well with the absorbance spectrum, with a slight shift in the maximum to 613 nm, likely due to the small amount of native phycocyanin in the preparation (Table 6). The SEC-HPLC monomer fraction of HTα-L11-β had spectroscopic properties similar to those of apo-HTα:holo-β monomers (Example A).

Effect of shortening the linker—A PCR-generated mutant, HTα-L9-β, with the linker Ala-(Gly)$_4$-Ser-(Gly)$_3$, was isolated in the course of producing the HTα-L11-β construct, where L11 is Ala-(Gly)$_4$-Ser-Gly-Ser-(Gly)$_3$. In other respects the two constructs were identical. Like the HTα-L11-β apoprotein (Ec320), the HTα-L9-β apoprotein (Ec319) was expressed in *E. coli* In high yield. HTα-L9-β (An319) isolated from *Anabaena* sp. exhibited the same, anomalous spectroscopic properties described above for the HTα-L11-β construct. Analysis of the HTα-L9-β protein by SEC-HPLC showed trimers and monomers in a ratio of 1:4, significantly lower than the ratio of 1:1 observed for HTα-L11-β. Since the extent of chromophorylation of trimer and monomer fractions of HTα-L9-β was similar to those of respective fractions of HTα-L11-β, the reduced trimer formation by HTα-L9-β may be a result of conformation change induced by the shorter linker between the subunits.

Expression of phycocyanin fusion proteins incorporating oligomerization domains—The dissociation of phycocyanins to the monomer at low protein concentration is highly undesirable when these proteins are used as fluorescent tags, particularly because of the resultant decrease in the number of PCB chromophores per tag. The finding that recombinant phycocyanin subunits with a 24-residue extension at the N-terminus fold and assemble in the same manner as native phycocyanin subunits (Example A, herein) suggested the introduction of the GCN4 oligomerization domains (60) at the subunit N-termini to produce stable phycocyanin oligomers. Expression of phycocyanin α subunit fused at the N-terminus to the trimerization domain GCN4 pII—The 33-residue peptide GCN4-pII forms homotrimeric parallel coiled coils with $K_D$<10$^{-9}$ M (60). Plasmid pBS314 (encoding HT-pII-α) was constructed to express a GCN4-pII-CpcA fusion (Table 4).

When HT-pII-α was expressed in *E.coli*, the recombinant protein was found almost entirely in inclusion bodies. Similar results were observed whether the induction was at 30 or 37° C. This behavior is in sharp contrast to that seen with HTα [Ec168; (Example A, herein)], where most of the recombinant protein remains soluble. A likely explanation is that trimerization of the GCN4-pII in the fusion protein is faster than the folding of the phycocyanin subunit domain and interferes with folding of the latter by promoting random aggregation of the partially folded subunit domains.

Cultures of *Anabaena* sp. PCC7120(pBS314) expressing HT-pII-α showed no negative phenotype, but had a bluer appearance than the wild type. Whole-cell absorbance spectra of *Anabaena* sp. PCC7120(pBS314) showed a higher ratio of phycocyanin:chlorophyll α. Whole-cell fluorescence was ~70% higher than that of the wild type or cells expressing HTα. Sucrose density gradient fractionation of *Anabaena* sp. PCC7120(pBS314) phycobilisome preparations showed that HT-pII-α represented a much higher proportion of the total phycocyanin in the trimer/hexamer fraction than in the intact phycobilisome fraction.

Over 40% of the phycobiliprotein in *Anabaena* sp. PCC7120(pBS314) cell lysate supernatant bound to the Ni$^{2+}$-NTA column and eluted with 200 mM imidazole. This was the highest relative level of recombinant phycobiliprotein of any of the His-tagged constructs we have expressed in the course of these studies. An314 bound much more tightly to the Ni$^{2+}$-NTA column than His-tagged phycocyanin constructs not containing oligomerization domains. The tightness of binding was evidenced by the slow desorption of the recombinant protein from the Ni$^{2+}$-NTA resin and the larger volume of imidazole buffer required for elution. Such behavior is to be anticipated from a molecule in which three polypeptides, each with a 6xHis tag, are trimerized through the GCN4-pII coiled coil. SDS-PAGE analysis showed that the An314 phycobiliprotein fraction was a stoichiometric HT-pII-α:β holoprotein complex. Chromatograplhy on SEC-HPLC showed that the HT-pII-α:β preparation was >75% trimer with some higher molecular weight component(s), presumably hexamer. Monomers were not detected.

The spectroscopic properties of (HT-pII-α:β)$_3$ are compared with those of the native C-phycocyanin trimer, (α:β)$_3$ in Table 6. The trimerized construct has significantly higher $A_{max}$:$A_{360\ nm}$ ratio than the native (α:β)$_3$ and a higher $\Phi_F$. Moreover, the absorbance spectrum of (HT-pII-α:β)$_3$ was unchanged at low protein concentrations where native phycocyanin, HTα:β, and α:HTβ were monomeric with significantly blue-shifted absorbance maxima and decreased $A_{max}$: $A_{360\ nm}$ ratios (Table 6; Example A, herein). Fluorescence polarization measurements provided an independent assessment of the stability of (HT-pII-α:β)$_3$ at low protein concentrations. In trimeric phycocyanin, the fluorescence polarization is very low because of rapid energy transfer among the nine phycocyanobilin chromophores. In contrast, in the phycocyanin monomer, the three PCBs are well separated and depolarization through energy transfer is minimized. Our data show that at high protein concentrations, where various phycocyanin preparations are trimeric, their fluorescence polarization is similar and low, with values of 0.035 to 0.070. The fluorescence polarization of HTα:β and α:HTβ, like that of native phycocyanin, rose sharply at very low protein concentrations, indicative of trimer dissociation. whereas that of (HT-pII-α:β)$_3$ was independent of protein concentration.

Expression of phycocyanin α subunit fused at the N-terminus to the tetramerization domain GCN4-pLI—The 33-residue peptide GCN4-pLI forms very stable homotetrameric parallel coiled coils (60). Several plasmids were constructed to express GCN4-pLI-α fusion proteins (Table 4), including plasmids pBS321 (encoding HT-pLI-α) and pBS323 (encoding HT-Strep2-pLI-α). The 10-residue Strep2 tag was incorporated into the HT-Strep2-pLI-α to test whether it would confer streptavidin-binding specificity on the construct.

When expressed in *E. coli*, GCN4-pLI-α fusion proteins, Ec321 (HT-pLI-α) and Ec323 (HT-Strep2-pLI-α), were mostly found in inclusion bodies. In contrast, when expressed in *Anabaena* sp. the fusion proteins An321 and An323 remained soluble. The yields of these His-tagged phycobiliproteins from this strain were high, reaching >20% of total phycobiliprotein. As described above for the GCN4-pII-α fusion proteins, the GCN4-pLI-α fusion protein (An321) bound very tightly to the Ni$^{2+}$-NTA resin. SDS-PAGE analysis showed that An321 protein fraction purified by IMAC had the composition of HT-pLI-α:β. Analysis by SEC-HPLC showed two components, a small amount of tetramer, (HT-pLI-α:β)$_4$, and the balance as a much larger component. The elution position of the latter lay outside the range of calibration of the size standards for the column, but extrapolation of the calibration curve allowed an estimate of the size of the larger component. The calculated molecular weight was consistent with that of a trimer of tetramers (Table 5).

Presumably, such a trimer would be formed by the interaction of three (HT-pLI-α:β)$_4$ assemblies through one of their phycocyanin α:β domains (while the other three α:β domains forming a trimer) in a manner analogous to that leading to the formation of (HT-pII-α:β)$_3$. In such a "trimer of tetramers", all α:β monomers are within phycocyanin trimers. Tetramers, each held together by a GCN4-pLI domain, would be the expected products of dissociation of such a "trimer of tetramers" at very low protein concentration. In accord with this expectation, the absorbance spectrum of HT-pLI-α:β at low protein concentration showed a $\lambda_{max}$ of 621 nm and an $A_{max}$:$A_{360\ nm}$ ratio of 7.5 (Table 6), values very similar to those obtained for (HT-pII-α:β)3 (see above).

HT-Strep2-pLI-α:β(An323) exhibited physical and spectroscopic properties identical to those of HT-pLI-α:β (An321) (Table 6), showing that the presence of the Strep2 sequence does not interfere with tetramerization by the GCN4-pLI domain.

Expression of subunit-fusion phycocyanins fused at the N-terminus to the trimerization domain GCN4-pII—As described above, His-tagged β-α subunit-fusion phycocyanin (An315) has spectroscopic properties identical to those of HTα:βand α:HTβ. Like those proteins, however, HT-β-L11-α also dissociates to monomers at high dilution. To increase utility of the HT-β-L11-α fusion phycocyanin as a fluorescent label, we fused the GCN4-pII domain to this construct to enhance trimer stability.

Plasmid pBS358 encodes HT-pII-β-L11-α (Table 4). When expressed in *E. coli*, HT-pII-β-L11-α apoprotein was found mostly in inclusion bodies, but when expressed in *Anabaena* sp. the HT-pII-β-L11-α protein remained soluble. Cultures of *Anabaena* sp. PCC7120(pBS358) had phenotypes very similar to those of the *Anabaena* sp. PCC7120 (pBS315) (see above), including the slower growth, "bluer" color, and increased whole-cell fluorescence. Analysis of phycobilisome preparations from this strain showed that HT-pII-β-L11-α was incorporated into the phycobilisomes. The 6xHis-tagged phycobiliprotein fraction (An358) purified by IMAC represented >22% of total cellular phycobilinroteins. As noted above for An314 (HT-pII-α:β) the An358 fraction also bound very tightly to the Ni2+-NTA resin.

SDS-PAGE analysis of the An358 fraction showed that it consisted >90% of HT-pII-β-L11-α along with a small amount of copurified wild-type phycocyanin α and β subunits (in a ratio of 1:1). Analysis by SEC-HPLC at protein concentrations <500 μg/ml, showed that HT-pII-β-L11-α preparation was largely trimeric with a small amount of a larger component (Table 5). Comparison of the spectroscopic properties of (HT-pII-β-L11-)3, purified by SEC-HPLC, with those of native C-phycocyanin trimer (α,β)3, showed no significant differences (Table 6). The absorbance spectrum of (HT-pII-b-L11-a)3 did not change with dilution to very low protein concentration (Table 6), indicating that the GCN4-pII domain prevented dissociation of the trimer.

The α-β fusion constructs purified from *Anabaena* sp., HTα-L9-β and HTα-L11-β, preferentially form monomers even at micromolar protein concentrations (see above). The similar construct incorporating the GCN4-pII domain, HT-pII-α-L11-β, is encoded by plasmid pBS362 (Table 4). The HT-pII-α-L11-β protein purified from *Anabaena* sp., An362, was found to be largely trimeric (84%) with the remainder hexameric (Table 5). No monomer was observed in the SEC-HPLC analysis. It is evident that the trimeric state of HT-pII-α-L11-β depends on trimerization of the GCN4-pII domain. Although remaining trimeric at low protein concentrations, the HT-pII-α-L11-β protein had spectroscopic properties similar to those of HTα-L11-β protein (Table 6), including the incomplete chromophorylation of the α domain.

Expression of recombinant phycocyanins with a tag conferring biospecificity—The constructs described above successfully address the requirement that the phycocyanin constructs maintain their oligomeric state at very low proteins concentrations. Next, we examine the introduction of an additional domain into such constructs, one which confers biospecific recognition. As a test case, we introduced a tag which binds specifically to streptavidin. Recombinant phycocyanins containing such a tag are immediately useful as reagents in the many applications of the widely used streptavidin-biotin methodologies (63).

Expression of Strep2-tagged phycocyanin constructs— The 10-residue Strep2 peptide forms complex with streptavidin with a $K_D$ of $7.2 \times 10^{-5}$ M (57). It is believed that the Step2 tag retains its affinity for streptavidin when fused either to an N- or C-terminus of a protein (57). Plasmids pBS327 and pBS323 were constructed to encode HT-Strep2-α and HT-Strep2-pLI-α. respectively (Table 4).

E. coli and Anabaena strains expressing either fusion protein were phenotypically identical to those expressing the corresponding non-Strep2-tagged proteins. Affinity-purified HT-Strep2-α:β (An327) and HT-Strep2-pLI-α:β (An323) proteins also had spectroscopic and aggregation properties very similar to corresponding non-Strep2-tagged proteins HTα:β (An168) and HT-pLI-α:β (An321) (Tables 5 and 6).

When blotted on a membrane, HT-Strep2-α (Ec327 and An327 and HT-Strep2-pLI-α (Ec323 and An323) were readily detected by probing with streptavidin-alkaline phosphatase conjugate, indicating that the Strep2 peptide sandwiched between the 6xHis tag and the GCN4-pLI domain still retains its affinity for streptavidin. When streptavidin-coated agarose beads were used as target, HT-Strep2-α:β holoprotein was largely removed from the beads on washing, a result anticipated from the low affinity of a single Strep2 tag for streptavidin [$K_D$=7.2×10$^{-5}$ M: (57)]. The HT-Strep2-pLI-α:β holoprotein, with its multiple Strep2 tags, bound much more strongly to the streptavidin-coated beads. This experiment demonstrates that oligomeric phycobiliprotein fusions with multiple Strep2 tags show the appropriate target specificity in streptavidin-based fluorescence assays.

Example C

Recombinant phycobiliprotein fusion proteins with carboxyl-terminal tagging.

We present here the in vivo production of biotinylated phycocyanin constructs that are readily usable in the many well-developed biotin/avidin applications (63). Materials and methods essentially as described in Example A or B are not restated.

Construction of expression plasmids—Plasmids coding for relevant protein fusion constructs are listed in Table 7. The expression vector pBS150v [(Example A); GenBank Accession number AF177932] was used to make plasmid pBS339v (4,677 bp) for expression to His-tagged proteins capable of being biotinylated in E. coli. The 7 codons between the 6xHis tag and the TEV site in pBS150v were replaced with the 21 codons specifying the BTN tag. The 13-residue sequence of the BTN tag was derived from the consensus sequence that can be biotinylated in E. coli (64). An AsuII restriction site was designed into the BTN sequence as a signature site to facilitate PCR product characterization and subsequent recognition of the BTN tag sequence. The NdeI-cpcA-HindIII fragment from pBS185 (Example A) was inserted between NdeI and HindIII sites of pBS339v, giving plasmid pBS329v (5,138 bp) encoding 6xHis- and BTN-tagged phycocyanin a subunit (Table 7). The BTN tag is positioned on the carboxyl-terminal side of the 6xHis tag, so that any recombinant molecules that have lost the biospecificity tag through proteolysis are not retained on the IMAC column. The NdeI-glbN-HindIII fragment from plasmid pGlbN (66) was similarly cloned to give plasmid pBS355, encoding 6xHis- and BTN-tagged cyanoglobin (Table 7). The same NdeI-HindIII fragment cloned into pBS t50v gave plasmid pBS121v (5,005 bp) encoding 6xHis-tagged cyanoglobin (Table 7).

The cloning vector pBS370v (4,589 bp) for expression of C-terminal Strep tagged proteins (Table 7) was derived from the cloning vector pBS152v [(Example A); GenBank accession No. AF177933] using inverse PCR. The 45-bp HindIII-BglI fragment at the end of the multiple cloning sites was replaced with the 68-bp HindIII-Strep-BglI sequence. An EheI site was engineered into the Strep tag coding sequence (56) as a signature site. Phycocyanin genes. in the form of NdeI-XmnI fragments from cognate plasmids (Example B) were inserted between NdeI and XmnI sites of pBS370v to generate phycocyanin-Strep tag fusions. The expression cloning vector pBS350v, an enhanced version of pBS152v, was created by replacing bp 3,801 to 4,070 of pBS152v with the 333-bp sequence described above.

DNA fragment encoding the 114-AA C-terminal portion of the Anabaena sp. PCC7120 BCCP protein (BCCP114) was amplified from Anabaena genomic DNA. The 0.36-kb PCR fragment was digested with EcoT22I and cloned into the EcoT22I site of pBS350v, giving plasmid pBS344v (4,977 bp). Again, phycocyanin genes, in the form of NdeI-XmnI fragments from cognate plasmids (Example B), were inserted between NdeI and XmnI sites of pBS344v to generate phycocyanin-BCCP114 fusion constructs with the BTN flexible linker. The 20-residue flexible linker between the two moieties was designed to (a) bear a thrombin recognition and cleavage site to allow separation of the fusion partners if so desired, and (b) be sufficiently long to allow packing of BCCP 114 on the outside of the rod substructures after the fusion protein is assembled in phycobilisomes (Example A, Example B). The GCN4-pII trimerization domain was introduced via modular cloning (Example B) between the 6xHis tag and the TEV protease site N' of the phycocyanin genes.

Expression of BTN-taggedfusion proteins—The 13-residue BTN tag has the consensus sequence of peptides found to be biotinylated in E. coli (64). Covalent attachment of a biotin to the Lys residue is apparently catalyzed by the biotin ligase encoded by the birA gene (65, 67). The BTN tag was fused to the N-terminus of the phycocyanin α subunit in an attempt to produice in vivo biotinylated phycocyanin. When the HT-BTN-α phycocyanin subunit, encoded by plasmid pBS329, was expressed in E. coli, the purified Ec329 protein was shown biotinylated in Western analysis. The same protein produced in Anabaena sp. PCC7120 (An329), however, was very poorly biotinylated, if at all, even when the culture medium had been supplemented with as much as 500 μM biotin. Two other assays for the presence of biotin on An329, competition with HABA {2-[(4'-hydra yphenyl)-azo]benzoic acid} for streptavidin in solution (68) and mobility shift in SEC-HPLC, indicated lack of biotinylation. Parallel results were obtained in a comparison of Ec317 (HT-BTN-pII-α) and An317 (HT-BTN-pII-α:β) proteins.

Sucrose density gradient experiments showed that both HT-BTN-α (An329) and HT-BTN-pII-α (An317) proteins were assembled into the phycobilisomes. To test whether the lack of An317 and An329 biotinylation in vivo was due to the fact that the recombinant phycocyanins were quickly assembled into the phycobilisome upon biosynthesis and therefore not available to the biotin ligase, the cyanoglobin (GlbN) protein from cyanobacterium Nostoc commune (66) was used. This myoglobin-like monomeric hemoprotein has a specific subcellular location around the periphery of the cytosolic face of the cell membrane (69), but is not membrane-bound. His-tagged cyanoglobins HT-GlbN and HT-BTN-GlbN (encoded by plasmids pBS121 and pBS355, respectively; Table 7) expressed in both E. coli and Anabaena sp. were found to have absorbance spectra nearly identical to that described for the native GlbN (70). However, while the Ec355 protein was found to be biotinylated, the An355 protein was not. The negative results for biotinylation in Anabaena sp. of all three different proteins tested, An317, An329, and An355, suggest that the BTN tag is not recognized by the Anabaena biotin ligase.

Analysis of the IMAC-purified An329 proteins by SDS-PAGE incated the composition HT-BTN-α:β. The An329

SEC-HPLC elution profile and spectroscopic characteristics were virtually identical to the non-BTN-tagged counterpart An168 (HTα:β; Table 8). The yield, however, was surprisingly low; An329 recovered by IMAC was <3% of total cellular phycobiliprotein, over 10-fold less than obtained for An168. This was also the case for An317 compared to its non-BTN-tagged counterpart An314 [HT-pII-α:β; (Example B)]. The yield of An355 was also dramatically lower than that of An121. These results suggest that the BTN tag destabilizes the tag-bearing proteins in *Anabaena* cells. Since An317 and An329 are assembled into the phycobilisomes, the latter may also be destabilized. Higher turnover of phycobilisomes and of An329 proteins in the cell may explain the observed phenotype of lower cellular phycobiliproteins in the strains *Anabaena* sp. PCC7120(pBS317) and *Anabaena* sp. PCC7120(pBS329).

Expression of truncated *Anabaena* BCCP114 protein— Since the BTN tag was not biotinylated in *Anabaena* sp., naturally occurring biotinylated proteins were investigated. A truncated gene encoding the C-terminal 114 residues of the *Anabaena* BCCP protein, covering the biotinylation domain (corresponding to the *E. coli* BCCP84 that is sufficient for enzyme-catalyzed biotinylation) and a large portion of the flexible linker, was amplified from the genome and cloned into pBS350, giving plasmid pBS344 (Table 7). Plasmid pBS344 encodes the 6xHis-tagged *Anabaena* BCCP114 with a long linker bearing the TEV and thrombin protease sites.

*E. coli* cultures expressing the 6xHis-tagged *Anabaena* BCCP114 protein (Ec344) grew normally, and produced very soluble Ec344 protein at >10 mg per liter of culture grown and induced at 37° C. The protein was shown biotinylated by Western analysis. Electrospray mass spectroscopy analysis suggested that about 20% of the Ec344 protein produced under these particular conditions was biotinylated. Growth and induction at 30° C. for longer period of time was attempted to increase the percentage of biotinylated holoprotein fraction of purified Ec344. However under these conditions, the yield of affinity purified protein was greatly decreased, possibly as a result of lowered production and increased degradation of the Ec344 protein.

Cultures of *Anabaena* sp. PCC7120(pBS344) expressing the An344 protein were fairly healthy, albeit having a slightly reduced level of total cellular phycobiliproteins. The yield of An344 protein, however, was quite low (usually <1 mg per liter of dense culture), possibly as a result of proteolytic clipping of the relatively long linker between the 6xHis tag and the BCCP114 domain. The An344 protein was shown to be biotinylated in Western analysis. Electrospray mass spectral analysis indicated that about 40% of the molecules were holo- (i.e., biotinylated) proteins, substantially higher than the fraction of those produced in *E. coli*. These results encouraged the study of C-terminal phycocyanin α and β fusions with BCCP 114.

Expression of phycocyanin β subunit-BCCP114 fusion proteins—Plasmid pBS353 encodes the fusion protein HTβ-BCCP114 (Table 7). Overexpression of Ec353 in *E. coli* gave high yield of the protein in soluble form. Since expression of Ec262 (HTβ) under similar conditions leads to substantial formation of inclusion bodies (Example A), the BCCP114 domain appears to enhance the solubility and folding of the fusion protein. The HTβ-BCCP 114 preparation from *E. coli* was found biotinylated in Western analysis.

Cultures of *Anabaena* sp. PCC7120(pBS353) generally had an unhealthy, yellowish green appearance, and the growth rate was at least 20% slower than that of the wild type even under high-light conditions. The yellowish green color of the cultures results from ~50% reduction of cellular phycocyanin as indicated by whole-cell absorption spectra. Upon IPTG induction of overproduction of the HTβ-BCCP114 protein, cultures in late-log growth frequently stopped growing, and further incubation of the culture often led to general cell lysis. This unexpected result, which was also observed with the HTα-BCCP114 construct (An351; see below), led to the abandonment of IPTG induction of *Anabaena* sp. PCC7120(pBS353) cultures. Expression of the HTβ-BCCP114 protein, therefore, was left to the leaky trc promoter (Example A), and generally resulted in a fairly low yield of An353 (<5% of total cellular phycobiliproteins). Nonetheless, very high cell densities could be obtained with these uninduced cultures.

The HTβ-BCCP114 protein was incorporated into phycobilisomes, with no obvious destabilizing effects. On SDS-PAGE analysis, however, the affinity-purified An353 protein had a substantially larger amount of the HTβ-BCCP114 subunit than the partner phycocyanin holo-α subunit, indicating a lowered stability of α:HTβ-BCCP114 as compared with that of α:HTβ. Also, a small fraction of the HTβ-BCCP114 preparation had lost the BCCP114 moiety by proteolysis.

On SEC-HPLC the An353 preparation separated into two major components. The larger component, with a retention time of about 12.4 min, had an apparent mass of 183.7 kDal, somewhat larger than 162.2 kDal calculated for the trimer, $(\alpha{:}HT\beta{-}BCCP114)_3$. On SDS-PAGE this larger fraction had only phycocyanin α and HTβ-BCCP114 subunits, in nearly 1:1 ratio. Upon exposure to $Zn^{2+}$, fluorescence from the HTβ-BCCP114 band under UV illumination was about twice as bright as that from the phycocyanin holo-α subunit, suggesting full bilin content (two PCBs per β) of the recombinant phycocyanin β subunit. The smaller component, eluted at ~14.4 min, contained mostly HTβ-BCCP114, with an apparent molecular weight corresponding to that of the homodimer, $(HT\beta{-}BCCP114)_2$. While this result is in accord with the observation that phycocyanin HTβ subunits can form stable homodimers (Example A), it also suggests that the HTβ-BCCP114 subunits have a lowered affinity for the phycocyanin α subunit, and may lose some of the α subunits during affinity purification.

Polypeptides in the HTβ-BCCP114 preparation lacking the BCCP114 portion represent a higher proportion of the fraction containing $(HT\beta{-}BCCP114)_2$ than of the $(\alpha{:}HT\beta{-}BCCP114)_3$ fraction. Such proteolytic removal of the BCCP114 domain of Ec353 was not observed in *E. coli*. The degradation observed in the preparations from *Anabaena* cells may therefore be the result of the much longer time the fusion protein An353 remains inside *Anabaena* cells, and may also reflect higher activity of *Anabaena* sp. proteases towards the long, thrombin site-bearing linker.

Spectroscopic properties of the trimeric fraction, $(\alpha{:}HT\beta{-}BCCP114)_3$, were similar to those of $(\alpha{:}HT\beta)_3$ (Table 8). The slightly blue-shifted $\lambda_{max}$ of $(\alpha{:}HT\beta{-}BCCP114)_3$ and the low $A_{max}{:}A_{360\ nm}$ ratio may reflect incomplete bilin addition to the β subunit, with a consequent perturbed conformation and lowered trimer stability in a portion of the preparation.

Western analysis showed that HTβ-BCCP114 produced in *Anabaena* sp. was biotinylated. Binding experiments with monomeric avidin-coated beads were performed to further assess the utility of An353 proteins as labels. When avidin molecules were in excess, ~30% of the An353 preparation could be immobilized on the beads and then specifically eluted, indicating a level of HTβ-BCCP114 biotinylation in

*Anabaena* sp. of about 30%. When an excess of An353 was used, saturation by the recombinant phycocyanin of nearly all of the biotin-binding sites on the avidin-coated beads was achieved. With appropriate excitation, the stained beads emitted brilliant red fluorescence.

Expression of HTβ-BCCP114fusion protein bearing the GCN4-pII trimerizattion domain—Only about a half of the HTβ-BCCP114 expressed in *Anabaena* retained the phycocyanin α subunit during purification. We had noted in earlier studies (Example B) that phycocyanin fusion proteins with GCN4-pII trimerization domains remained trimeric even at very low protein concentrations and contained both subunits in stoichiometric amounts. This is most likely attributable to the greatly increased local concentration of subunits.

HT-pII-β-BCCP114, encoded by plasmid pBS359 (Table 7), was expressed at high level in *E. coli*. About 25% of Ec359 could be isolated in soluble form, much more than seen with pII-phycocyanin subunit fusion constructs (Example B), again showing the increase in solubility attributable to the presence of the BCCP114 domain (see above).

Cultures of *Anabaena* sp. PCC7120(pBS359) were yellowish, similar to those of *Anabaena* sp. PCC7120 (pBS353), with an even slower growth rate. However, such cultures grew to very high cell densities after IPTG induction.

The HT-pII-β-BCCP114 protein was assembled into phycobilisomes with no obvious destabilizing effect. In contrast to An353, affinity-purified An359 protein preparation had the HT-pII-β-BCCP114 subunit and the phycocyanin holo-α subunit in a 1:1 ratio. The yield ol An359 was surprisingly low, generally <2% of total cellular phycobiliproteins. Almost no HT-pII-β lacking the BCCP114 moiety was observed, suggesting that in the stable trimers. (α:HT-pII-β-BCCP114)$_3$, the long linker between β and BCCP114 is shielded from proteases.

On SEC-HPLC, the An359 protein preparation migrates as a component with an apparent mass of 475.2 kDal, significantly higher than the 350.3 kdal calculated for a hexamer, [(α:HT-pII-β-BCCP114)$_3$]$_2$. A phycocyanin hexamer is normally formed by face-to-face stacking of two trimers (42). A model of the (α:HT-pII-β-BCCP114)$_3$ trimer reveals that a hexamer could form by two trimers stacking on the BCCP114 face, with the BCCP114 domains on the outside of the trimer rings. Such a hexamer would have a larger radius of gyration and exhibit a higher apparent mass on SEC. It should be noted that at very low protein concentration the hexamer is expected to dissociate into trimers. Spectroscopic properties of (α:HTβ-BCCP114)$_3$ (Table 8), were very similar to those of GCN4-pII-bearing constructs such as (HT-pII-α:β)$_3$.

Western analysis showed that HT-pII-β-BCCP114 obtained from *Anabaena* sp. was biotinylated. The utility of this construct as a fluorescent label was explored in binding experiments with avidin-coated beads. With avidin in excess, about 75% of (α:HT-pII-β-BCCP114)$_3$ was immobilized on the beads and then specifically eluted off. The extent of biotinylation of the BCCP114 domain in HT-pII-β-BCCP114 proteins is presumably ~30%. similar to that seen in HTβ-BCCP114 (An353). The higher binding percentage is anticipated. since only one of the three BCCP114 domains needs to be biotinylated for the entire trimer to bind to the beads. When an excess amount of (α:HT-pII-β-BCCP114)$_3$ was used, the amount of α:HT-pII-β-BCCP114 monomer equivalents immobilized was nearly 2.5-fold that of monomeric avidins. Under phycocyanin excitation, (α:HT-pII-β-BCCP114)$_3$-stained avidin- and streptavidin-coated beads were highly fluorescent.

Expression of phycocyanin-BCCP114 fusion protein with covalently bridged α and β subunits—Constructs with covalently bridged α and β subunits provide a way of ensuring 1:1 α:β stoichiometry, as demonstrated earlier with the HTα-L11-β construct (Example B). HTα-L11-β-BCCP114 encoded by plasmid pBS361 (Table 7) was expressed well in *E. coli* and acceptably in *Anabaena* sp.

HTα-L11-03-BCCP114 protein was assembled into the phycobilisome. As with HTα-L11-β (Example B), such phycobilisomes were less stable. The affinity-purified An361 fraction represented ~10% of total cellular phycobiliprotein and consisted >90% of HTα-L11-β-BCCP114. A small amount of native phycocyanin α and β subunits copurified with HTα-L11-β-BCCP114, indicating that the α and β subunits in the fusion construct retained their ability to interact with native subunits. A small fraction of the HTα-L11-β-BCCP114 proteins had lost the BCCP114 portion by proteolysis.

SEC-HPLC fractionation showed that the An361 preparation consisted of trimers and monomers in an ~1:1 ratio. Spectroscopic properties of the trimers, (HTα-L11-β-BCCP114)$_3$, were found very similar to those of (HTα-L11-β)$_3$ (Table 8), indicating that carboxyl terminal attachment to BCCP114 did not perturb the phycocyanin subunit domains. In a related construct. involving a carboxyl terminal fusion of the α subunit, (HTα-L11-β)$_3$, bilin addition to the α subunit domain was shown to be very incomplete (Example B). Since (HTα-L11-β)$_3$ and (HTα-L11-β-BCCP114)$_3$ have virtually identical spectroscopic properties (Table 8), bilin addition to the α subunit domain of (HTα-L11-β-BCCP114)$_3$ is presumably also incomplete.

The HTα-L11-β-BCCP114 protein preparation from *Anabaena* sp. was shown to be biotinylated in Western analysis. In binding experiments with streptavidin- and avidin-coated beads, the An361 preparation gave results similar to those obtained with HTβ-BCCP114 (see above), indicating ~30% biotinylation of the BCCP domain of HTα-L11-β-BCCP114.

Expression ofphycocyanin-BCCP114 fusion protein with covalently bridged α and β subunits and the GCN4-pII trimerization domain—Plasmid pBS365 was constructed to encode the HT-pII-α-L11-β-BCCP114 (Table 7). Unlike Ec362 (HT-pII-α-L11-β) which is found almost entirely in inclusion bodies (Example B), Ec365 expressed in *E. coli* remained soluble, again indicating the solubility-promoting effect of the BCCP114 domain.

HT-pII-α-L11-β-BCCP114, expressed in *Anabaena* sp. PCC7120(pBS365), was found to be assembled into the phycobilisome. The yield of affinity-purified An365 was >5% of total cellular phycobiliprotein. The An365 preparation consisted of >90% HT-pII-α-L11-β-BCCP114 with a small amount of copurifying native phycocyanin α and β subunits. Virtually no loss of the BCCP114 moiety was observed.

On SEC-HPLC, the An365 preparation was found to consist mostly of hexamers, with a small fraction of trimers. (HT-pII-α-L11-β-BCCP114)$_3$ had spectroscopic properties similar to those of (HT-pII-α-L11-β)$_3$ (Table 8), again consistent with incomplete bilin addition to the phycocyanin α domain (Example B).

The An365 from *Anabaena* sp. was shown to be biotinylated in Western analysis and gave results in binding experiments with monomeric avidin-coated beads quantitatively similar to those obtained with An359, (α:HT-pII-β-BCCP114)$_3$. Streptavidin-coated beads stained with excess of An365 appeared blue and emitted brilliant red fluorescence under appropriate excitation.

Expression of phycocyanin α subunit-BCCP114 fusion proteins—Recombinant phycocyanin α subunits, with the amino-terminus fused to polypeptides of varying length, display unmodified bilin content and spectroscopic properties (Example A, Example B). As noted above, fusions at the carboxyl terminus of the α subunit interfered with bilin addition. To examine whether this behavior is specific to particular C-terminal fusions or is general, four phycocyanin α-BCCP114 fusion constructs analogous to the β-BCCP fusions described above were prepared (Table 7).

Expression of the four constructs, Ec351, Ec357, Ec360, and Ec364, in *E. coli* gave results very similar to those observed with the four corresponding phycocyanin β-BCCP114 constructs (see above). Expression of the four α-BCCP114 constructs in *Anabaena* sp., however, gave very different results.

An351 (HTα-BCCP114) represented <0.5% of total cellular phycobiliprotein. SDS-PAGE showed that the HTα-BCCP114 polypeptide had a very low bilin content, indicating that the BCCP114 extension on the α subunit greatly interferes with bilin addition. The low yield is likely attributable to the ease of proteolysis of the apo-HTα-BCCP114 polypeptide. The An351 preparation contained little phycocyanin β subunit, suggesting reduced affinity to the apo-HTα-BCCP114. The proteolytic cleavage of the long peptide linker between α and BCCP114 was also high in the apo-HTα-BCCP114 polypeptide. An351 preparations often contained a substantial amount of degradation product of HTα-BCCP114 in which the BCCP114 moiety had been clipped off. The extremely low yield of An351 also suggests that the protein is rapidly turned over in the cell.

Results from expression of An357 (Table 7) were nearly identical to those from An351, except that the native phycocyanin β subunit was copurified with the (mostly apo-) HT-pII-α-BCCP114 subunit in nearly 1:1 ratio. Results from expression of An360 (HTβ-L11-α-BCCP114) and An364 (HT-pII-β-L11-α-BCCP114) were very similar. The yield was ~5% of total cellular phycobiliprotein, substantially higher than that obtained from An351 and An357. A large percentage of the purified fusion protein, however, had lost the BCCP114 moiety. These results showed that interference with bilin addition to the phycocyanin α-subunit domain was a feature common to all of these different BCCP114 fusion constructs.

Expression of phycocyanin α subunit-Strep tag fusion proteins—To address the question of the possible dependence of bilin addition to the phycocyanin α subunit on the size of the carboxyl-terminal fusion partner, such fusions were prepared with the 10-residue Strep tag (Table 7).

The yield of the His-tagged protein preparation, An386, from *Anabaena* sp. PCC7120(pBS386) expressing HTα-Strep was <1% of total cellular phycobiliprotein (in great contrast to >30% usually obtained from cells expressing HTXα). On SEC-HPLC the An386 preparation runs almost entirely as monomer, with a very small amount of trimers. The monomer peak contained HTα-Strep and native phycocyanin β in nearly 1:1 ratio. While the β subunit was the normal holoprotein, the HTα-Strep subunits were almost entirely apo-subunits. The apo-HTα-Strep appeared to have lowered affinity for the phycocyanin β subunit, as indicated by the observation that fractions collected from the trailing part of the monomer peak on SEC-HPLC were enriched in the apo-HTα-Strep subunit relative to the holo-β subunit. The spectroscopic properties of the HTα-Strep:β monomer were very similar to those of the apo-HTα:holo-β monomer (Table 8; Example A), including the characteristic broad peak in the fluorescence excitation spectra. Thus, even a short extension on the carboxyl terminus of phycocyanin α subunit affects the posttranslational bilin addition.

Expression of phycocyanin fusion protein with covalently bridged α and β subunits and the Strep tag—In a final attempt to address the problem of incomplete bilin addition in carboxyl terminal fusions of the phycocyanin α-subunit, we examined behavior of HTβ-L11-α-Strep fusions (encoded by plasmid pBS394; Table 7). The yield of affinity-purified An394 was ~10% of total cellular phycobiliprotein. Unlike the An315 preparation (from cells expressing HTβ-L11-α) that consists mostly of trimers, the An394 proteins is mostly monomeric, with small amounts of trimeric and hexameric components. Proteins in the higher assembly states had a higher bilin content, with those in the hexamer fraction approaching three PCBs per HTβ-L11-α-Strep molecule, i.e., holoproteins. Proteins in the monomer fraction on average contained two PCBs per HTβ-L11-α-Strep molecule, most likely lacking the α subunit bilin. In total, <10% of the polypeptides in the An394 preparation carried bilin on the α subunit domain, a small but significant improvement over the HTα-Strep:β construct. Most An394 preparation could be immobilized on streptavidin-coated beads, showing that the Strep tag in the HTβ-L11-α-Strep molecules has retained its affinity for streptavidin and is available for binding.

TABLE 1

Properties of Anabaena sp. PCC7120 and derivative strains and of expression vectors carried by these strains relevant to the production of His-tagged C-phycocyanin α and β subunits

| Strain and vector[a] | Strain genomic characteristics | Polypeptide construct encoded on vector |
|---|---|---|
| PCC7120(pBS168) | Wild-type | HTα |
| PCC7120(pBS262) | Wild-type | HTβ |
| B646(pBS168) | cpcBAC[b] has a transposon inserted between the promoter and the cpcB open reading frame | HTα |
| B646(pBS262) | cpcBAC | HTβ |
| B64328(pBS168) | cpcE[c] inactivated by transposon insertion | HTα |
| B64328(pBS262) | cpcE | HTβ |
| B64407(pBS168) | cpcF[c] inactivated by transposon insertion | HTα |
| B64407(pBS262) | cpcF | HTβ |

TABLE 1-continued

Properties of Anabaena sp. PCC7120 and derivative strains and of expression vectors carried by these strains relevant to the production of His-tagged C-phycocyanin α and β subunits

| Strain and vector[a] | Strain genomic characteristics | Polypeptide construct encoded on vector |
|---|---|---|
| PCC7120(pBS167) | Wild-type | HTα$^{A12T}$ |
| PCC7120(pBS162) | Wild-type | HTβ$^{S46G,N76D}$ |

[a]The expression vectors, specified in parentheses, are derived from pBS150v and pBS150 as described in the text.
[b]Genes cpcB and cpcA encode the β and α subunits of C-phycocyanin and cpcC encodes a linker polypeptide involved in the assembly of trimers (αβ)$_3$ and hexamers [(αβ)$_3$]$_2$ and their assembly into phycobilisomes (5, 6).
[c]cpcE and cpcF encode two subunits of a heterodimeric phycocyanin α subunit lyase required for the addition of phycocyanobilin to the apophycocyanin α subunit (1, 2–4).

TABLE 2

Molecular weights of His-tagged phycocyanins in different aggregation states, as determined by size exclusion chromatography and by analytical ultracentrifugation.

| Protein[a] | SEC-HPLC (kDa) | AUC (kDa) | Major Components | Aggregation state | Expected MW (kDa) |
|---|---|---|---|---|---|
| Native PC | 211.7 | | α:β | Hexamer | 225.7 |
| | 124.7 | | | Trimer | 112.8 |
| | 44.5 | | | Monomer | 37.6 |
| An168 | 301.6 | | HTα:β | Hexamer | 243.0 |
| | 145.3 | 125.9 | | Trimer | 121.5 |
| | 49.2 | 34.8 | | Monomer | 40.5 |
| An262 | 136.9 | 121.9 | α:HTβ | Trimer | 121.5 |
| | 62.4 | 43.4 | | Monomer | 40.5 |
| An168-BAC | 289.3 | | HTα:β | Trimer | 243.0 |
| | 137.2 | | | Monomer | 121.5 |
| | 17.3 | | HTα | Subunit monomer | 20.9 |
| An262-BAC | 50.3 | | HTβ | Subunit homodimer | 45.0 |
| An168-E/F | 106.8 | | Apo-HTα:β | Trimer | 119.7 |
| | 29.8 | | | Monomer | 39.9 |
| An262-E/F | 54.1 | | HTβ | Subunit homodimer | 45.0 |
| | 33.8 | | Apo-α:HTβ | Monomer | 39.9 |

[a]"-BAC" suffix indicates proteins isolated from cpcBAC mutant strains of Anabaenea sp., and "-E" and "-F" indicate proteins isolated from cpcE and cpcF mutant strains of Anabaena sp., respectively.

TABLE 3

Spectroscopic properties of His-tagged phycocyanins[a].

| Sample | Abs$^{max}$ (nm) | Ex$^{max}$ (nm) | Em$^{max}$ (nm) | εm (M$^{-1}$cm$^{-1}$) (×1,000) | Φ$_f$ |
|---|---|---|---|---|---|
| Native PC (α:β)$_3$ | 615–618 | 615 | 644 | 929 ± 2.1 | 0.27 ± 0.06 |
| (HTα:β)$_3$ | 615–621 | 618 | 642 | 921 ± 36 | 0.22 ± 0.05 |
| (α:HTβ)$_3$ | 615–619 | 616 | 642 | 888 ± 33 | 0.23 ± 0.04 |
| HTα | 618–622 | 615 | 637 | 109 ± 2.5 | 0.23 ± 0.02 |
| (HTβ)$_2$ | 605 | 606 | 639 | 365 ± 13 | 0.22 ± 0.03 |
| apo-HTα:β | 607 | 606 | 642 | 182 ± 1.4 | 0.24 ± 0.00 |
| One protein-bound PCB | 660[b] | — | — | 35.40 | 0 |
| | 280 | — | — | 14.85 ± 0.1 | |

TABLE 4

Expression plasmids with specific functional domains in the encoded protein

| Plasmid[a] | Affinity tag | Biospec. tag[b] | Coiled coil domain | Protease site | Core protein |
|---|---|---|---|---|---|
| pBS311 | 6xHis | | GCN4pII | TEV | LacZ$^\alpha$ |
| pBS314 | 6xHis | | GCN4pII | TEV | CpcA |
| pBS319 | 6xHis | | | TEV | CpcA-L9-CpcB |
| pBS320 | 6xHis | | | TEV | CpcA-L11-CpcB |
| pBS362 | 6xHis | | GCN4pII | TEV | CpcA-L11-CpcB |
| pBS315 | 6xHis | | | TEV | CpcB-L11-CpcA |
| pBS358 | 6xHis | | GCN4pII | TEV | CpcB-L11-CpcA |
| pBS283 | | Strep2 | | TEV | LacZ$^\alpha$ |
| pBS342 | 6xHis | Strep2 | | TEV | LacZ$^\alpha$ |
| pBS327 | 6xHis | Strep2 | | TEV | CpcA |
| pBS303 | | Strep2 | GCN4pLI | TEV | LacZ$^\alpha$ |
| pBS309 | 6xHis | Strep2 | GCN4pLI | TEV | LacZ$^\alpha$ |
| pBS323 | 6xHis | Strep2 | GCN4pLI | TEV | CpcA |
| pBS312 | 6xHis | | GCN4pLI | TEV | LacZ$^\alpha$ |
| pBS321 | 6xHis | | GCN4pLI | TEV | CpcA |

[a]Like the parent plasmids pBS150v and pBS150, all plasmids listed have two versions: the smaller one, indicated in the text with a suffix "v", is more suitable for cloning manipulations, but is lacking the 3.7-kb pDU1HC fragment that enables autonomous plasmid replication in Anabaena sp. PCC7120 (Example A, herein).
[b]The biospecificity tag is positioned on the carboxyl-terminal side of the 6xHis tag, so that any recombinant molecules that have lost the biospecificity tag through proteolysis are not retained on the IMAC column. The Strep2 tag is a 10-residue peptide with specific affinity for streptavidin.

TABLE 5

Determination of apparent molecular weight of components in recombinant phycocyanin preparations by SEC-HPLC[a]

| Protein | Calc. mass (kDa) | Percent area | Assembly state[b] | Theoretical mass (kDa)[c] |
|---|---|---|---|---|
| An168 | 49.2 | 5 | Monomer | 40.5 |
| (HT$\alpha$:$\beta$) | 145.3 | 95 | Trimer | 121.5 |
| An327 | 44.2 | 4 | Monomer | 41.4 |
| (HT-Strep2-$\alpha$:$\beta$) | 137.9 | 94 | Trimer | 124.3 |
| | 275.4 | 2 | Hexamer | 248.7 |
| An314 | 110.2 | 79 | Trimer | 132.7 |
| (HT-pII-$\alpha$:$\beta$) | 406.0[d] | 21 | (Hexamer)$_2$ | 530.7 |
| An321 | 232.8 | 13 | Tetramer | 176.9 |
| (HT-pLI-$\alpha$:$\beta$) | 499.5[d] | 81 | (Tetramer)$_3$ | 530.7 |
| An323 | 264.0 | 6 | Tetramer | 182.7 |
| (HT-Strep2-pLI-$\alpha$:$\beta$) | 429.3[d] | 94 | (Tetramer)$_3$ | 548.2 |
| An319 | 35.8 | 79 | Monomer | 41.0 |
| (HT$\alpha$-L9-$\beta$) | 99.3 | 19 | Trimer | 122.9 |
| | 232.6 | 2 | Hexamer | 245.8 |
| An320 | 34.1 | 49 | Monomer | 41.1 |
| (HT$\alpha$-L11-$\beta$) | 89.7 | 46 | Trimer | 123.4 |
| | 213.6 | 5 | Hexamer | 246.7 |
| An362 | 128.9 | 84 | Trimer | 134.5 |
| (HT-pII-$\alpha$-L11-$\beta$) | 304.7[d] | 15 | Hexamer | 269.1 |
| An315 | 107.9 | 76 | Trimer | 123.4 |
| (HT$\beta$-L11-$\alpha$) | 235.7 | 23 | Hexamer | 246.7 |
| An358 | 115.6 | 64 | Trimer | 134.5 |
| (HT-pII-$\beta$-L11-$\alpha$) | 587.2[d] | 35 | (Hexamer)$_2$ | 538.0 |

[a]For experimental conditions, see text.
[b]By convention, the $\alpha$:$\beta$ heterodimer is referred to as a phycocyanin "monomer."
[c]Values are for holo-proteins.
[d]Apparent molecular weight outside the range defined by the calibration standards.

TABLE 6

Spectroscopic properties of phycocyanin constructs[a]

| Sample[b] | Initial assembly state | $\lambda_{max}$[c] (nm) | $A_{max}/A_{360\,nm}$ | $Ex_{max}$ (nm) | $Em_{max}$ (nm) | $\epsilon_M$ (M$^{-1}$cm$^{-1}$) | $\Phi_f$ |
|---|---|---|---|---|---|---|---|
| Denatured PC | $\alpha$:$\beta$ | 280 | — | — | — | 44,550[d] | |
| | | 660 | 1.0 | — | — | 106,200 | 0 |
| Native PC | ($\alpha$:$\beta$)$_3$ | 615–619 | 6.4 | 615 | 644 | 929,000 | 0.27 |
| An168 | (HT$\alpha$:$\beta$)$_3$ | 615–621 | 6.4 | 618 | 642 | 921,000 | 0.22 |
| An327 | (HT-Strep2-$\alpha$:$\beta$)$_3$ | 615–619 | 6.4 | 618 | 642 | 922,000 | 0.23 |
| An262 | ($\alpha$:HT$\beta$)$_3$ | 615–619 | 6.3 | 616 | 642 | 888,000 | 0.23 |
| An314 | (HT-pII-$\alpha$:$\beta$)$_3$ | 621–622 | 7.5 | 622 | 642 | 927,000 | 0.39 |
| An321 | (HT-pLI-$\alpha$:$\beta$)$_4$ | 621–623 | 7.5 | 621 | 643 | 1,231,000 | 0.28 |
| An323 | (HT-Strep2-pLI-$\alpha$:$\beta$)$_4$ | 621–623 | 7.2 | 621 | 644 | 1,240,000 | 0.27 |
| An315 | (HT$\beta$-L11-$\alpha$)$_3$ | 615–622 | 6.2 | 622 | 643 | 900,000 | 0.21 |
| An358 | (HT-pII-$\beta$-L11-$\alpha$)$_3$ | 619–621 | 6.7 | 620 | 643 | 915,000 | 0.29 |

TABLE 6-continued

Spectroscopic properties of phycocyanin constructs[a]

| Sample[b] | Initial assembly state | $\lambda_{max}$[c] (nm) | $A_{max}/A_{360\,nm}$ | $Ex_{max}$ (nm) | $Em_{max}$ (nm) | $\epsilon_M$ (M$^{-1}$cm$^{-1}$) | $\Phi_f$ |
|---|---|---|---|---|---|---|---|
| An320 | (HTα-L11-β)$_3$ | 605–608 | 5.2 | 613 | 643 | 677,000[e] | 0.22 |
| An362 | (HT-pII-α-L11-β)$_3$ | 607–610 | 5.8 | 615 | 642 | 707,000[f] | 0.24 |

[a]Trimer or tetramer components obtained by SEC-HPLC were used for all measurements. $A_{max}:A_{360\,nm}$ values, excitation maxima ($Ex_{max}$), emission maxima ($Em_{max}$), and quantum yields of fluorescence ($\Phi_f$) are given for measurements at protein concentrations ≦0.05 mM. $\epsilon_M$ values are given for measurements on the components specified in column 2 at protein concentrations >1 μM.
[b]Properties of proteins not described in this study are taken from Example A, herein.
[c]$\lambda_{max}$ values were determined at protein concentrations from 0.05 to 3 μM. Where the spectra shift to the blue with decreasing protein concentration, the limits of $\lambda_{max}$ values are those measured at the lowest and highest concentrations, respectively.
[d]Absorbance from the three protein-bound PCBs only, excluding contribution from Tyr and Trp residues (Example A, herein).

TABLE 7

List of fusion constructs indicating order of domains

| Fusion construct[a] | Plasmid[b] |
|---|---|
| 6xHis-BTN-TEV-LacZ$^{\alpha'}$ | pBS339 |
| 6xHis-BTN-TEV-CpcA | pBS329 |
| 6xHis-BTN-pII-TEV-CpcA | pBS317 |
| 6xHis-BTN-TEV-GlbN | pBS355 |
| 6xHis-TEV-GlbN | pBS121 |
| 6xHis-TEV-TBN-BCCP114 | pBS344 |
| 6xHis-TEV-CpcB-TBN-BCCP114 | pBS353 |
| 6xHis-GCN4pII-TEV-CpcB-TBN-BCCP114 | pBS359 |
| 6xHis-TEV-CpcA-L11-CpcB-TBN-BCCP114 | pBS361 |
| 6xHis-GCN4pII-TEV-CpcA-L11-CpcB-TBN-BCCP114 | pBS365 |
| 6xHis-TEV-CpcA-TBN-BCCP114 | pBS351 |
| 6xHis-GCN4pII-TEV-CpcA-TBN-BCCP114 | pBS357 |
| 6xHis-TEV-CpcB-L11-CpcA-TBN-BCCP114 | pBS360 |
| 6xHis-GCN4pII-TEV-CpcB-L11-CpcA-TBN-BCCP114 | pBS364 |
| 6xHis-TEV-Strep | pBS370 |
| 6xHis-TEV-CpcA-Strep | pBS386 |
| 6xHis-TEV-CpcB-L11-CpcA-Strep | pBS394 |

[a]Functional domains in each construct are listed in order from N- to C-terminus, with particularly relevant domains in bold face. CpcA and CpcB correspond to the α and β subunits of phycocyanin, respectively.
[b]All plasmids have two versions. The smaller one, indicated in the text with a suffix "v", is for cloning and expression in E. coli, and lacks the 3.7-kb pDU1HC fragment that enables autonomous plasmid replication in Anabaena sp. PCC7120 (Example A).

TABLE 8

Spectroscopic properties of phycocyanin constructs[a]

| Sample | Initial assembly state[b] | $\lambda_{max}$ (nm)[c] | $A_{max}/A_{360\,nm}$ | $Ex_{max}$ (nm) | $Em_{max}$ (nm) | $\epsilon_M$(M$^{-1}$cm$^{-1}$) | $\Phi_f$ |
|---|---|---|---|---|---|---|---|
| Denatured PC | α:β | 280 | — | — | — | 44,550[d] | 0 |
|  |  | 660 | 1.0 | — | — | 106,200 | 0 |
| Native PC | (α:β)$_3$ | 615–619 | 6.4 | 615 | 644 | 929,000 | 0.27 |
| An168 | (HTα:β)$_3$ | 615–621 | 6.4 | 618 | 642 | 921,000 | 0.22 |
| An329 | (HT-BTN-α:β)$_3$ | 615–618 | 6.4 | 617 | 642 | 920,000 | 0.22 |
| An386 | HTα-Strep:β | 605–609 | 5.6 | 607 | 639 | 186,000 | 0.19 |
| An262 | (α:HTβ)$_3$ | 615–619 | 6.3 | 616 | 642 | 888,000 | 0.23 |
| An353 | (α:HTβ-BCCP$^{114}$)$_3$ | 611–616 | 5.7 | 612 | 642 | 896,000 | 0.21 |
| An314 | (HT-pII-α:β)$_3$ | 621–622 | 7.5 | 622 | 642 | 927,000 | 0.39 |
| An317 | (HT-BTN-pII-α:β)$_3$ | 621–622 | 7.3 | 622 | 644 | 939,000 | 0.31 |
| An359 | (α:HT-pII-β-BCCP$^{114}$)$_3$ | 619–622 | 6.6 | 621 | 643 | 915,000 | 0.29 |
| An320 | (HTα-L11-β)$_3$ | 605–608 | 5.2 | 613 | 643 | 677,000[e] | 0.22 |
| An361 | (HTα-L11-β-BCCP$^{114}$)$_3$ | 605–606 | 5.3 | 604 | 637 | 664,000[e] | 0.23 |

TABLE 8-continued

Spectroscopic properties of phycocyanin constructs[a]

| Sample | Initial assembly state[b] | $\lambda_{max}$ (nm)[c] | $A_{max}/A_{360\ nm}$ | $Ex_{max}$ (nm) | $Em_{max}$ (nm) | $\epsilon_M(M^{-1}cm^{-1})$ | $\Phi_f$ |
|---|---|---|---|---|---|---|---|
| An362 | (HT-pII-α-L11-β)$_3$ | 607–610 | 5.8 | 615 | 642 | 707,000[f] | 0.24 |
| An365 | (HT-pII-α-L11-β-BCCP$^{114}$)$_3$ | 605–607 | 5.5 | 606 | 641 | 692,000[f] | 0.27 |

[a]Properties of constructs not described in this studies are taken from the accompanying studies (Example A, Example B).
[b]Affinity-purified proteins were futher purified by SEC-HPLC, and collected fractions in 50 mM Na-phosphate pH 7.0 buffer ± 1 mM NaN$_3$ were used for all measurements. $A_{max}:A_{360\ nm}$ values, excitation maxima ($Ex_{max}$), emission maxima ($Em_{max}$), and quantum yields of fluorescence ($\Phi_f$) are given for measurements at protein concentrations $\leq 0.05$ μM. $\epsilon_M$ values are given for measurements on the components specified in column 2 at protein concentrations >1 μM.
[c]$\lambda_{max}$ values were determined at protein concentrations from 0.05 to 3 μM. Where the spectra shift to the blue with decreasing protein concentration, the $\lambda_{max}$ values are those measured at the lowest and highest concentrations, respectively.
[d]Absorbance from the three protein-bound PCBs only, corrected for contributions from Tyr and Trp residues (Example A).
[e]The phycocyanin α subunit domain has an average PCB content of ~0.5.
[f]The phycocyanin α subunit domain has an average PCB content of ~0.25.

REFERENCES FOR EXAMPLES A, B and C.

1. Fairchild, C. D., et al. (1992) *Proc. Natl. Acad. Sci. USA* 89, 7017–7021
2. Fairchild, C. D. and Glazer, A. N. (1994) *J. Biol. Chem.* 269, 8686–8694
3. Swanson, R. V., et al. (1992) *J. Biol. Chem.* 267, 16146–16154
4. Zhou, J., et al. (1992) *J. Biol. Chem.* 267, 16138–16145
5. Belknap, W. R., and Haselkorn, R. (1987) *EMBO J.* 6, 871–884
6. Swanson, R. V., deLorimier, R., and Glazer, A. N. (1992) *J. Bacteriol.* 174, 2640–2647
7. Cai, Y. A., Schwartz, S. H., and Glazer, A. N. (1997) *Photosynthesis Res* 53, 109–120
8. Porath, J., Carlsson, J., Olson, I., and Belfrage, G. (1975) *Nature* 258, 598–599
9. Cai, Y. A., Murphy, J. T., and Glazer, A. N. (1999) Example B, herein.
10. Cai, Y. A. and Glazer, A. N. (1999) Example C, herein.
11. Hanahan, D. (1983). *J. Mol. Biol.* 166, 557–580
12. Hu, N. T., Thiel, T., Gidding, T. H., and Wolk, C. P. (1981) *Virology* 114, 236–246
13. Wolk, C. P., et al. (1984) *Proc. Natl. Acad. Sci. U.S.A.* 81, 1561–1565
14. Sambrook, J., Fritsch, E. F., and Maniatis, T. (1989) *Molecular Cloning: A Laboratory Manual*. Cold Spring Harbor Laboratory Press, Cold Spring Harbor, N.Y.
15. Cai, Y. A. and Wolk, C. P. (1990) *J. Bacteriol.* 172, 3138–3145
16. Mullis, K. B. and Faloona, F. (1987) *Methods Enzymol.* 155, 335–350
17. Yanisch-Perron, C., Vieira, J. and Messing, J. (1985) *Gene* 33, 103–10
18. Frank, G., et al. (1978) *Hoppe-Seyler's Physiol. Chem.* 359, 1491–1507
19. Apt, K. E., Collier, J. L., and Grossman, A. R. (1995) *J. Mol. Biol.* 248, 79–96
20. Balbas, P., et al. (1986) *Gene* 50, 3–40
21. Banner, D. W., Kokkinidis, M., and Tsernoglou, D. (1987) *J. Mol. Biol.* 196, 657–675
22. Bancroft, I., and Wolk, C. P. (1989) *J. Bacteriol.* 171, 5949–5954
23. Dougherty, W. G., Carrington, J. C., and Parks, T. D. (1988) *EMBO J.* 7, 1281–1287
24. Parks, T. D., et al. (1994) *Anal. Biochem.* 216, 413–417
25. Brosius, J., Dull, T. J., Sleeter, D. D., and Noller, H. F. (1981) *J. Mol. Biol.* 148, 107–127
26. Walton, D. K., Gendel, S. M., and Atherly, A. G. (1992) *Nucl. Acids Res.* 20, 4660–4660
27. Whorff, L. L. and Gloden, J. W. (1993) GenBank Accession Number L23221
28. Yamanaka, et al. (1978) *J. Biol. Chem.* 253, 8303–8310
29. Bryant, D. A., Glazer, A. N., and Eiserling, F. A. (1976). *Arch. Microbiol.* 110, 61–75
30. Laemmli, U. K. (1970) *Nature* 227, 680–685
31. Berkelman, T. R. and Lagarias, J. C. (1986) *Anal. Biochem.* 156, 194–201
32. Lakowicz, J. R. (1983). *Principles of Fluor. Spectroscopy*. Plenum Press, New York
33. Parker, C. A. and Rees, W. T. (1960) *The Analyst* 85, 587–600
34. Glazer, A. N., Fang, S., and Brown D. M. (1973) *J. Biol. Chem.* 248, 5679–5685
35. Glazer, A. N. and Fang, S. (1973) *J. Biol. Chem.* 248, 659–662
36. Riordan, J. F., Wacker, W. E. C., and Vallee, B. L. (1965) *Biochemistry* 4, 1758–1765
37. Beaven, G. H. and Holiday, E. R. (1952) *Adv. Protein Chem.* 7, 319–386
38. Shackleton, C. H. L., et al. (1990) *J. Chromatogr.* 562, 175–190
39. Schirmer, T., et al. (1985) *J. Mol. Biol.* 184, 257–277
40. DeLange, R. J., Williams, L. C., and Glazer, A. N. (1981) *J. Biol. Chem.* 256, 9558–9566
41. Sidler, W., et al. (1986) *Hoppe-Seyler's Biol. Chem.* 367, 627–642
42. Duerring, M., Schmidt, G. B., and Huber, R. (1991) *J. Mol. Biol.* 217, 577–592
43. Kleywegt, G. J. (1996) *Acta Cryst.* D52, 842–857
44. Jones, T. A., Zou, J.-Y., Cowan, S. W., Kjeldgaard, M. (1991) *Acta Cryst.* A 47, 110–119

45. Brünger, A. T. (1992) *X-PLOR Manual Version* 3.1, Yale University Press, New Haven.
46. Brünger, A. T. (1992) *XPLOR—A System for Crystallography and NMR* 3.1 edit. Yale University Press, New Haven.
47. Laskowski, R. A., et al. (1993). *J. Appl. Crystallogr.* 26, 282–291
48. Glazer, A. N. (1985) *Annu. Rev. Biophys. Biophys. Chem.* 14, 47–77
49. Glazer, A. N. (1988) *Methods Enzymol.* 167, 291–303
50. Debreczeny, M. P., et al. (1993) *J. Phys. Chem.* 97, 9852–9862
51. Klotz, A. V., Leary, J. A., and Glazer, A. N. (1986) *J. Biol. Chem.* 261, 15891–15894
52. Klotz, A. V. and Glazer, A. N. (1987) *J. Biol. Chem.* 262, 17350–17355
53. Yu, M.-H. and Glazer, A. N. (1982) *J. Biol. Chem.* 257, 3429–3433
54. Schirmer, T., et al. (1986) *J. Mol. Biol.* 188, 651–676
55. de Lorimier, R., Wilbanks, S. M., and Glazer, A. N. (1993) *Plant Mol. Biol.* 21, 225–237
56. Schmidt, T. G. M. and Skerra, A. (1994) *J. Chromatogr. A* 676, 337–345
57. Schmidt, T. G. M., et al. (1996) *J. Mol. Biol.* 255, 753–766
58. Hope, I. A. and Struhl, K. (1986) *Cell* 46, 885–896
59. O'Shea, E. K., Klemm, J. D., Kim, P. S., and Alber, T. (1991) *Science* 254, 539–544
60. Harbury, P. B., Zhang, T., Kim, P. S., and Alber, T (1993) *Science* 262, 1401–1407
61. Parks, D., Herzenberg, L., and Herzenberg, L. (1997) *Cytometry*, 29,328–339
62. Toole, C. M., et al. (1998) *Mol. Microbiol.* 32, 475–486
63. Wilchek, M. and Bayer, E. A. (eds) (1990) Avidin-Biotin Technology. *Methods Enzymol.* vol. 184. Academic Press, New York
64. Schatz, P. J. (1993) *Bio/Technology* 11, 1138–1143
65. Beckett, D., Kovaleva, E., and Schatz, P. J. (1999) *Protein Sci.*, 8, 921–929.
66. Potts, M., et al. (1992) *Science* 256, 1690–1692
67. Howard, P. K., Shaw, J., and Otsuka, A. J. (1985) *Gene* 35, 321–331
68. Green, N. M. (1970) *Methods Enzymol.* 18A, 418–424
69. Hill, D. R., et al. (1996) *J. Bacteriol.* 178, 6587–6598
70. Thorsteinsson, M. V., et al. (1996) *Biochim. Biophys. Acta* 1292, 133–139

FURTHER EXAMPLES

1. Phycobiliproteins carrying the GCN4-pII or the GCN4-pLI coiled-coil oligomerization domain.

These fusion proteins were found almost entirely in inclusion bodies in *E. coli*, but found incorporated in the phycobilisome in *Anabaena* sp. These constructs, as well as other examples discussed below, all show that proteins bearing the GCN4 oligomerization domains are found almost entirely in inclusion bodies when expressed in *E. coli*, but are incorporated in phycobilisomes when expressed in *Anabaena* sp. Upon phycobilisome dissociation, good yields of soluble, fluorescently tagged proteins are obtained.

2. Streptavidin-phycocyanin α subunit fusion proteins.

The core streptavidin (stvC) gene used here encodes a StvC corresponding to residues 16 to 133 of the mature streptavidin. Recombinant StvC with a 24-residue N-terminal extension bearing a 6xHis tag and the TEV site. HT-StvC (encoded by plasmid pBS282), was expressed relatively poorly in *E. coli*, with about 80% of the proteins found in inclusion bodies. The StvC-CpcA fusion protein has an 11-residue bridge linking the two moieties. HT-StvC-CpcA (encoded by plasmid pBS292) was produced at relatively high level in *E. coli*, but was found only in inclusion bodies.

The fusion protein An292 was well expressed in *Anabaena* sp. $Ni^{2+}$-NTA-purified soluble An292 protein accounted for >15% of total cellular phycobiliproteins. The An292 protein was of HT-StvC-α:β in composition, ran on SEC-HPLC as tetramer (HT-StvC-α:β)4 and trimer of tetramers [(HT-StvC-α:β)4]3, similar to the finding with An321 with phycocyanin α subunit bearing the tetramerization domain GCN4-pLI: (HT-pLI-α:β)4 and [(HT-pLI-α:β)4]3. An292 also had spectroscopic properties virtually identical to those of An321, making it an excellent fluorescent label. The An292 protein was assembled into phycobilisomes and also found to bind biotin.

Like streptavidin tetramers, the (HT-StvC-α:β)4 tetramer was much more stable than the (HT-pLI-α:β)4 tetramer. On room temperature denaturing SDS-PAGE, (HT-StvC-α:β)4 released only the β subunits and retained the (HT-StvC-α)4 aggregate. The tetramer could be broken only by boiling the protein before loading on SDS-PAGE. Purified phycobilisomes displaying StvC had a tendency to aggregate out of solution, likely a direct result of inter-phycobilisome linkage mediated by tetramerization of the monomeric StvC domains displayed on PBS. Usually within 48 hrs all such phycobilisomes precipitated out of solution.

3. Protein A-phycocyanin α subunit fusion proteins.

Expression of truncated protein A (SpA) in the cytosol of *E. coli* has been shown to give very poor yield, with particularly severe proteolysis occuring to the hinge of domains A and B. In our construct, the truncated SpA protein [denoted SpA(DABC)] contains the hinge of domain E. domains D, A, and B in entirety, and domain C lacking a small portion of its hinge. Domains D. A, B and C all retain their IgG-binding structure. Plasmid pBS356 encodes the recombinant SpA with a C-terminal 6xHis tag extending from the residual hinge region of domain C: SpA(DABC)-6xHis. The protein, Ec356, was obtained in extremely poor yield when expressed in *E. coli*, regardless whether the purification method was denaturing (using guanidine HCl; see e.g., Example B, supra) or not, and almost no full-length Ec356 protein was seen on SDS-PAGE. Recombinant protein A with engineered hinge regions has been described for better expression of the SpA in *E. coli*. Without such extensive reengineering, *E. coli* is not an appropriate organism for expression and production of recombinant protein A.

In experiments described here, the SpA(DABC) protein is fused at its C-terminus to the phycocyanin a subunit through a 24-residue linker bearing a 6xHis tag and a recognition and cleavage site for the specific TEV endoprotease. The fusion protein, SpA(DABC)-6xHis-TEV-CpcA, encoded by plasmid pBS349, was obtained in very poor yield when expressed in *E. coli*, likely a result of extensive proteolysis. Little full-length Ec349 protein was seen, with most of the Ni2+-NTA-purified protein having some or all of the IgG-binding domains missing.

When expressed in *Anabaena* sp., the fusion protein An349 was found assembled into phycobilisomes with no apparent destabilizing effect on the light-harvesting complex. Cellular phycobiliprotein level relative to chlorophyll α, however, was about 20% lower, suggesting an elevated phycobiliprotein turnover. Nonetheless, growth rate of cultures under high-light intensity was not affected. Ni2+-NTApurified An349 proteins were obtained in relatively low yield of about 5% of total cellular phycobiliproteins.

On SEC-HPLC, the An349 proteins fractionated into two components: >80% as the trimer (SpA-6xHis-α:β)3 and the rest being SpA-6xHis-α subunit. SDS-PAGE showed that the SpA moiety of the majority of the fusion protein had also been proteolyzed, giving full-length SpA(DABC)-6xHis-α (49.5 kDal; ca. 10%), SpA(ABC)-6xHis-α (41.5 kDal; ca. 20%), and SpA(BC)-6xHis-α (35.5 kDal; ca. 70%). No proteolytic cleavage on domain B hinge [giving SpA(C)-6xHis-α] and domain C hinge (giving 6xHis-α) was observed. The lack of proteolytic cleavage on the domain B hinge is a clear indication of different protease activities in *Anabaena* sp. because that hinge region has been found to be the most susceptible to proteolytic cleavage in *E. coli*. The lack of clipping in the domain C hinge is likely due to its proximity to the phycobilisome, minimizing access by proteases. This hinge region is susceptible to proteolytic activities in *Anabaena* sp. when displayed farther away from the phycobilisome surface (see below).

SDS-PAGE also showed that the carrier phycocyanin α domain had the normal bilin content. The SEC-HPLC trimer (SpA-6xHis-α:β)3 fraction had spectroscopic properties very similar to those of (6xHis-α:β)3, with absorbance maximum at 616 nm, an A616 nm:A360 nm ratio of 6.1, fluorescence excitation maximum at 618 nm (for 650 nm emission), and fluorescence emission maximum at 641 nm (for 560 nm excitation).

An349 proteins were tested for their ability to bind IgG in ELISA. Serially diluted An349 protein was immobilized on a 96-well plate and then allowed to bind to mouse IgG-alkaline phosphatase conjugate. After thorough washing, the alkaline phosphatase activity was assayed by catalyzed color development. In such semi-quantitative assays the SpA-6xHis-α:β fusion protein had about 30% IgG-binding activity as compared to commercially obtained protein A (Sigma Chemical Co.) with all five IgG-binding domains.

Another SpA-phycocyanin α fusion protein was constructed to enhance the fusion protein's utility. This construct is similar to the SpA(DABC)-6xHis-TEV-CpcA construct described above, but has the 33-residue GCN4-pII trimerization domain inserted between the 6xHis tag and the TEV site. This fusion protein, SpA(DABC)-6xHis-pII-TEV-CpcA, encoded by plasmid pBS354, was found only in inclusion bodies when expressed in *E. coli*. Unlike Ec349, about 10% of the Ec354 proteins affinity-purified from inclusion bodies was full-length [SpA(DABC)-6xHis-pII-TEV-CpcA], suggesting fast sequestering of the newly synthesized polypeptides into inclusion bodies due to bundling by the GCN4-pII domain. The majority of purified Ec354 proteins, however, were still missing some or all of the SpA IgG-binding domains, again illustrating protein A's susceptibility to *E. coli* proteases.

When expressed in *Anabaena* sp., the fusion protein An354 was found assembled into phycobilisomes with no apparent destabilizing effect on the complex. Interestingly, cells expressing An354 had a more normal phenotype than those expressing An349 (see above). Ni2+-NTA-purified An354 proteins were obtained in reasonable yield, accounting for >7% of total cellular phycobiliproteins.

On SEC-HPLC, the An354 protein ran as a single peak with an apparent molecular weight corresponding to a hexamer, [(SpA-6xHis-pII-α:β)3]2. SDS-PAGE confirmed the composition as SpA-6xHis-pII-α:β, and showed that most of the SpA moiety was subject to proteolytic clipping at different hinge regions, giving full-length SpA(DABC)-6xHis-pII-α (53.2 kdal; ca. 10%), SpA(ABC)-6xHis-pII-α (45.2 kDal; ca. 20%), SpA(BC)-6xHis-pII-α (39.2 kDal: ca. 50%), and 6xHis-pII-α (25.2 kdal; ca. 20%). The complete removal of the displayed SpA protein by cleavage in the domain C hinge is not seen with the An349 protein, and is likely a result of the SpA moiety in An354 being displayed farther away from the phycobilisome surface. As with An349, no proteolytic cleavage on domain B hinge [giving SpA(C)-6xHis-pII-α] was observed in *Anabaena* sp. Different fractions collected from the An354 SEC-HPLC peak had identical distributions of the fusion proteins missing various IgG-binding domains, consistent with the view that the fusion proteins are displayed on the phvcobilisome as monomers (with respect to the GCN4-pII domain), and only form GCN4-pII-bundled stable trimers after cell lysis and phycobilisome dissociation.

SDS-PAGE also showed that the carrier phycocyanin α domain had the normal level of phycocyanobilin. The SEC-HPLC hexamer [(SpA-6xHis-pII-α:β)3]2 fraction had spectroscopic properties very similar to those of (6xHis-pII-α:β)3 (see, e.g. Example C, supra), with an absorbance maximum at 621 nm, an A616 nm:A360 nm ratio of 7.5, fluorescence excitation maximum at 621 nm (for 650 nm emission), and fluorescence emission maximum at 642 nm (for 560 nm excitation). These favorable spectroscopic properties of such GCN4-pII-bundled stable trimers make the fusion protein a good fluorescent tag. ELISA also showed that An354 had IgG-binding affinity comparable to commercially obtained protein A. The increased IgG-binding activity of An354 in ELISA compared to An349 may be a result of more protein being immobilized on the 96-well plate, and/or cooperative binding of GCN4-pII-bundled SpA proteins. Such oligomerization-induced binding affinity increase has been observed (see e.g. Examples B and C, supra).

4. Cyanoglobin fusion to phycocyanin α or β subunit.

Cyanoglobin (GlbN) is a 15.7-kDal monomeric hemoprotein produced in the cyanobacterium Nostoc commune. This protein contains a non-covalently linked heme, and is well expressed as soluble protein in both *E. coli* (expression at 30° C. and 37° C.) and *Anabaena* sp. when bearing a 24-residue N-terminal extension containing a 6xHis tag and the TEV recognition and cleavage site (recombinant protein encoded by plasmic pBS121; Example C, supra). However, recombinant cyanoglobin with C-terminal extension (the stop codon is replaced by a Ser codon) was found unable to fold normally in *E. coli*. Cyanoglobin-phycocyanin subunit fusion constructs, GlbN-6xHis-TEV-CpcA (encoded by plasmid pBS190) and GlbN-6xHis-TEV-CpcB (encoded by plasmid pBS274), gave relatively poor yield and were found mostly in inclusion bodies when expression was carried out at 37° C. At 30° C., the two fusion proteins had somewhat different behavior. Although both were still fast degraded in *E. coli* (thus giving low yield), the GlbN-HTa fusion protein (Ec190) was produced in a substantial amount as soluble protein, with apparently normal amount of heme and an absorbance spectrum identical to that of 6xHis-tagged GlbN (Ec121). The GlbN-HTb fusion protein (Ec274), on the other hand, was still found mostly in inclusion bodies, with the small amount of soluble proteins purified largely as apoproteins (without heme). These results indicate that the C-terminal extensions have slowed the folding of GlbN in *E. coli*, and the cyanoglobin domain in the GlbN-HTh fusion protein appears to be misfolded.

*Anabaena* cultures expressing either fusion proteins were healthy, showing no negative phenotypes at all. Both fusion proteins, An190 and An274, were found assembled into phycobilisomes with no destabilizing effect on the macrostructures, were purified in high yield (each accounting for >20% of total cellular phycobiliproteins) with cognate partner subunits in 1:1 ratio, and found to have spectroscopic properties very similar to native phycocyanin.

The cyanoglobin moiety in the fusion proteins, however, behaved quite differently. Using phycocyanin α subunit as the carrier domain (An190), the displayed GlbN domain was <30% holo when eluted off the Ni2+-NTA column, and lost almost all of the bound heme upon dialysis to remove imidazole. Using the phycocyanin β subunit as the carrier domain (An274), most of the displayed GlbN domain was purified with bound heme, and the heme remained bound to GlbN after dialysis. No degradation of the cyanoglobin domain was observed in either An190 or An274 in *Anabaena* cells, suggesting that the cyanoglobin domain displayed on the N' of phycocyanin α subunit was misfolded but remained resistant to proteolysis. The misfolded GlbN domain appears to interfere with the carrier domain's formation of phycocyanin trimers: on SEC-HPLC, about 80% of An190 proteins ran as trimers, (GblN-HT α:β)3, while the rest ran as monomers, GblN-HT α:β, in contrast to An168 which runs only as trimers, (HT α:β)3. Like An262, (α:HTβ)3, An274 ran only as trimers, (α:GlbN-HTβ)3, on SEC-HPLC.

In sum, both fusion proteins were quickly degraded in *E. coli*, but well displayed on phycobilisomes in *Anabaena* sp. Cyanoglobin displayed on the of phycocyanin β subunit seemed to fold better than on the N-terminus of the α subunit, and was able to retain larger amount of heme than the latter during purification. No degradation of the cyanoglobin domain was observed in either construct in *Anabaena* cells, suggesting that the cyanoglobin domain displayed on the N-terminus of phycocyanin α subunit was misfolded but remained resistant to proteolysis.

5. Sperm whale myoglobin fusion to phycocyanin α or β subunit.

The myoglobin from sperm whale (SWMβ) is similar to cyanoglobin as a monomeric protein with non-covalently bound heme. SWMβ with a C-terminal extension of only six His residues (SWMβ-6xHis; encoded by plasmid pBS114) can be well expressed as soluble holoprotein in both *E. coli* and *Anabaena* sp. Recombinant SWMβ proteins with larger C-terminal extensions, however, appear to be unable to fold. SWMβ-6xHis-TEV-LacZ$^a$ (encoded by plasmid pBS261), SWMβ-6xHis-TEV-CpcA (encoded by plasmid pBS271), and SWMb-6xHis-TEV-CpcB (encoded by plasmid pBS318) fusion proteins all gave poor yields when expressed in *E. coli* and were found nearly entirely in inclusion bodies.

*Anabaena* cultures expressing either An271 (SWMβ-HTα) or An361 (SWMβ-HTβ) fusion proteins were healthy, and the fusion proteins were found assembled into phycobilisomes, and were purified with cognate partner phycocyanin subunits. Although myoglobin displayed on the N-terminus of phycocyanin β subunit (SWMβ-HTβ) gave slightly better yield of the full length protein (with little amount of bound heme), both fusion proteins were purified mostly without the myoglobin moiety. This indicates that the displayed domain, if unable to fold, is degraded.

6. Maltose-binding protein (MalE, MBP) fusion to phycocyanin α or β subunit.

The "mature" recombinant MalE protein (lacking the membrane-crossing signal peptide) with a C-terminal 6xHis tag is well expressed as a soluble protein in the cytosol of both *Anabaena* sp. and *E. coli*. In the MalE-phycocyanin fusion constructs, the last three residues (Arg-Ile-Thr) of the mature MalE are replaced by the spacer Asn-Ser-Ser, and this modified MalE is fused to the N-teiminus of a phycocyanin subunit via a 24-residue linker that bears a 6xHis tag and a recognition and cleavage site for the TEV protease. The MalE-6xHis-TEV-α (Ec396) and MalE-6xHis-TEV-β (Ec398) fusion proteins are both expressed as soluble proteins in *E. coli* in relatively high yield.

The strain *Anabaena* sp. PCC7120(pBS396) expressing fusion protein MalE-6xHis-TEV-α had a phenotype very similar to that of strain *Anabaena* sp. PCC7120(pBS168) expressing HTα. Sucrose density gradient sedimentation fractionation showed that the MalE-6xHis-TEV-α fusion protein was assembled into the phycobilisome without obvious effects on the macromolecular complex. $Ni^{2+}$-NTA affinity-purified protein, An396, was in relatively good yield, accounting for >10% of total cellular phycobiliproteins. Over 95% of the An396 proteins can bind to, and be specifically eluted from amylose columns, diagnostic of functional MalE.

SDS-PAGE showed that the An396 protein has the composition MalE-6xHis-TEV-α:β, and Zn2+-induced fluorescence indicates full chromophorylation of phycocyanin carrier domain. SEC-HPLC showed that An396 protein was monomeric, (MalE-6xHis-TEV-α:β) a behavior differing from that of HTα:β, whose elution volume is that of a trimer. The MalE-6xHis-TEV-α:β protein in the SEC-HPLC monomer peak fraction, however, has spectroscopic properties very similar to the (HTα:β)3 trimer, with absorbance maximum at 617 nm, fluorescence excitation maximum at 618 nm (for 650 nm emission), fluorescence emission max. at 637 nm (for 560 nm excitation), and a fluorescence quantum yield of 0.23.

Upon digestion with the TEV protease, over 90% of purified MalE-6xHis-TEV-α:β protein can be clipped at the TEV recognition site to separate the displayed domain (MalE) from the phycocyanin carrier domain.

The fusion protein MalE-6xHis-TEV-β is expressed in *Anabaena* sp. at a level (>7.5% of total cellular phycobiliproteins) comparable to that of MalE-6xHis-TEV-α (An396). Over 95% of Ni2+-NTA-purified An398 protein can bind to, and then be specifically eluted from, the amylose resin, indicative of the MalE function. However, analysis of An398 by SDS-PAGE shows that the protein preparation consists mostly of MalE-6xHis-TEV-β with only a very small amount of the partner phycocyanin α subunit. Zn2+-induced fluorescence suggests that the MalE-6xHis-TEV-β protein has a full complement of phycocyanobilin, i.e., two PCBs per β subunit domain. On SEC-HPLC most of the preparation runs as (MalE-6xHis-TEV-β)2 homodimer, with a slight shoulder corresponding to the (α:MalE-6xHis-TEV-β) monomer. Like MalE-6xHis-TEV-α:β (An396), virtually all of the MalE-6xHis-TEV-β fusion proteins can be cleaved at the TEV site to separate the displayed protein (MalE) and the carrier protein (phycocyanin β subunit).

The MalE-6xHis-TEV-β protein is found to be assembled into phycobilisomes without obvious deleterious effect on the latter structures. Since assembly of the fusion protein into the phycobilisomes requires association with the phycocyanin α subunit, this result indicates that the MalE-6xHis-TEV-β fusion protein has a reduced affinity to the α subunit which is likely lost during the purification process. In the absence of α subunits, phycocyanin β subunits have been shown to form stable homodimers (see. e.g. Example A, supra). Such interference by the displayed domain on the phycocyanin subunit carrier domain's affinity for its cognate partner subunit is likely fusion protein specific—cyanoglobin displayed on the N-terminus of the phycocyanin β subunit does not appear to have obvious effects on the fusion protein's affinity for the phycocyanin α subunit.

The (MalE-6xHis-TEV-β)2 homodimer peak fraction in SEC-HPLC was used for spectroscopic characterization. Similar to the (HTβ)2 homodimer protein, the (MalE-6xHis-TEV-β)2 homodimer has absorbance and fluorescence excitation maxima at 605 nm, a fluorescence emission maximum at 638 nm, and a fluorescence quantum yield of 0.26.

To obtain 1:1 α:β stoichiometry, the β-L11-α subunit-fusion phycocyanin (Example B. supra) can be used, in place of the β subunit, as a carrier protein. Constructs incorporating the GCN4-pII trimerization domain, such as (MalE-6xHis-pII-α:β)3 and (MalE-6xHis-pII-β-L11-α)3, have excellent spectroscopic properties, and are very useful, for instance, in studies of protein glycosylation.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cell comprising a functional oligomeric phycobiliprotein comprising a fusion protein comprising a functional displayed domain and a functional phycobiliprotein domain, wherein the fusion protein further comprises in addition to the functional displayed domain (a) a specific binding moiety selected from a streptavidin biotin-binding moiety, a biotinylated or biotinylatable moiety, and an antigen binding immunoglobulin moiety; or (b) a protease cleavage site between the displayed domain and the phycobiliprotein domain.

2. The cell of claim 1, wherein the phycobiliprotein domain is a natural phycobiliprotein domain.

3. The cell of claim 1, wherein the functional oligomeric phycobiliprotein is an α,β heterodimer.

4. The cell of claim 1, wherein the displayed domain comprises a moiety selected from the group consisting of an affinity tag, an oligomerization moiety, a specific binding moiety, and a signaling moiety.

5. The cell of claim 1, wherein the fusion protein comprises a specific binding moiety selected from a streptavidin biotin-binding moiety, a biotinylated or biotinylatable moiety, and an antigen binding immunoglobulin moiety.

6. The cell of claim 1, wherein the fusion protein further comprises a linker peptide between the displayed domain and the phycobiliprotein domain.

7. The cell of claim 1, wherein the fusion protein comprises a protease cleavage site between the displayed domain and the phycobiliprotein domain.

8. The cell of claim 1, wherein the phycobiliprotein domain comprises at least one functionally attached bilin.

9. The cell of claim 1, wherein the displayed domain is refractive to expression in *E. coli*.

10. The cell of claim 1, wherein the oligomeric phycobiliprotein is assembled in a functional phycobilisome.

11. The cell of claim 1, wherein the oligomeric phycobiliprotein provides a fluorescent tag.

12. The cell of claim 1, wherein the displayed domain is transparent to wavelengths of visible light absorbed by phycobiliproteins.

13. The cell of claim 1, wherein the displayed domain is transparent to wavelengths of energy emitted by the phycobiliprotein domain.

14. The cell of claim 1, wherein the cell is or is a progeny of a cell which naturally expresses a phycobiliprotein.

15. The cell of claim 1, wherein the cell is a cyanobacterium.

16. The cell of claim 1, wherein the cell is a rhodophyte (red algae).

17. The cell of claim 1, wherein the cell is a cryptomonad.

18. The cell of claim 1, wherein the cell is an *Anabaena* cell.

19. The cell of claim 1, which comprises a polynucleotide encoding the fusion protein, and produces the oligomeric phycobiliprotein.

* * * * *